US012213835B2

(12) United States Patent
McLaughlin et al.

(10) Patent No.: US 12,213,835 B2
(45) Date of Patent: Feb. 4, 2025

(54) ULTRASOUND IMAGING SYSTEM FOR GENERATION OF A THREE-DIMENSIONAL ULTRASOUND IMAGE

(71) Applicant: Bard Access Systems, Inc., Salt Lake City, UT (US)

(72) Inventors: William Robert McLaughlin, Bountiful, UT (US); Steffan Sowards, Salt Lake City, UT (US); Anthony K. Misener, Bountiful, UT (US)

(73) Assignee: Bard Access Systems, Inc., Salt Lake City, UT (US)

( * ) Notice: Subject to any disclaimer, the term of this patent is extended or adjusted under 35 U.S.C. 154(b) by 0 days.

(21) Appl. No.: 17/501,909

(22) Filed: Oct. 14, 2021

(65) Prior Publication Data

US 2022/0117582 A1    Apr. 21, 2022

Related U.S. Application Data

(60) Provisional application No. 63/092,368, filed on Oct. 15, 2020.

(51) Int. Cl.
*A61B 8/08*    (2006.01)
*A61B 8/00*    (2006.01)

(52) U.S. Cl.
CPC ............ *A61B 8/466* (2013.01); *A61B 8/0841* (2013.01); *A61B 8/4254* (2013.01); *A61B 8/483* (2013.01); *A61B 8/5215* (2013.01); *A61B 8/56* (2013.01)

(58) Field of Classification Search
CPC ..... A61B 8/466; A61B 8/0841; A61B 8/4254; A61B 8/483; A61B 8/5215; A61B 8/56;
(Continued)

(56) References Cited

U.S. PATENT DOCUMENTS 4,311,138 A    1/1982  Sugarman
4,971,068 A   11/1990  Sahi
(Continued)

FOREIGN PATENT DOCUMENTS

AU    2006201646 A1    11/2006
CN       114129137 B     9/2022
(Continued)

OTHER PUBLICATIONS

Ikhsan Mohammad et al: "Assistive technology for ultrasound-guided central venous catheter placement", Journal of Medical Ultrasonics, Japan Society of Ultrasonics in Medicine, Tokyo, JP, vol. 45, No. 1, Apr. 19, 2017, pp. 41-57, XPO36387340, ISSN: 1346-4523, DOI: 10.1007/S10396-017-0789-2 [retrieved on Apr. 19, 2017].

(Continued)

*Primary Examiner* — Alexei Bykhovski
(74) *Attorney, Agent, or Firm* — Rutan & Tucker LLP

(57) ABSTRACT

An ultrasound imaging system configured to generate a 3D ultrasound image of a target area is disclosed herein. The ultrasound imaging system includes a console including one or more processors and non-transitory computer readable medium having stored thereon one or more logic modules. The ultrasound imaging system further includes an ultrasound probe, configured to acquire a plurality of ultrasound images of a target area, the ultrasound probe coupled to the console by an ultrasound probe connector having optical fiber including one or more core fibers, the ultrasound probe being a point of reference for the console to generate a three-dimensional visualization by stitching together the plurality of ultrasound images, starting from the point of reference.

12 Claims, 7 Drawing Sheets

(58) Field of Classification Search
CPC ......... A61B 5/062; A61B 5/066; A61B 5/067; A61B 5/489; A61B 5/6824; A61B 5/743; A61B 8/4444; A61B 8/12; A61B 8/461; A61B 2017/3413; A61B 2034/2048; A61B 2034/2051; A61B 2034/2061; A61B 2034/2072; A61B 2090/378; A61B 8/4245; A61B 8/4263; A61B 8/085; A61B 8/4472; A61B 8/5246; A61B 8/5292; G01S 7/52082; G01S 15/8993; G02B 6/02042

See application file for complete search history.

(56) References Cited

U.S. PATENT DOCUMENTS

| | | |
|---|---|---|
| 5,148,809 A | 9/1992 | Biegeleisen-Knight et al. |
| 5,181,513 A | 1/1993 | Touboul et al. |
| 5,325,293 A | 6/1994 | Dorne |
| 5,441,052 A | 8/1995 | Miyajima |
| 5,549,554 A | 8/1996 | Miraki |
| 5,573,529 A | 11/1996 | Haak et al. |
| 5,775,322 A | 7/1998 | Silverstein et al. |
| 5,879,297 A | 3/1999 | Haynor et al. |
| 5,908,387 A | 6/1999 | LeFree et al. |
| 5,967,984 A | 10/1999 | Chu et al. |
| 5,970,119 A | 10/1999 | Hofmann |
| 6,004,270 A | 12/1999 | Urbano et al. |
| 6,019,724 A | 2/2000 | Gronningsaeter et al. |
| 6,068,599 A | 5/2000 | Saito et al. |
| 6,074,367 A | 6/2000 | Hubbell |
| 6,129,668 A | 10/2000 | Haynor et al. |
| 6,132,379 A | 10/2000 | Patacsil et al. |
| 6,216,028 B1 | 4/2001 | Haynor et al. |
| 6,233,476 B1 | 5/2001 | Strommer et al. |
| 6,245,018 B1 | 6/2001 | Lee |
| 6,263,230 B1 | 7/2001 | Haynor et al. |
| 6,375,615 B1 | 4/2002 | Flaherty et al. |
| 6,436,043 B2 | 8/2002 | Bonnefous |
| 6,498,942 B1 | 12/2002 | Esenaliev et al. |
| 6,503,205 B2 | 1/2003 | Manor et al. |
| 6,508,769 B2 | 1/2003 | Bonnefous |
| 6,511,458 B2 | 1/2003 | Milo et al. |
| 6,524,249 B2 | 2/2003 | Moehring et al. |
| 6,543,642 B1 | 4/2003 | Milliorn |
| 6,554,771 B1 | 4/2003 | Buil et al. |
| 6,592,520 B1 | 7/2003 | Peszynski et al. |
| 6,592,565 B2 | 7/2003 | Twardowski |
| 6,601,705 B2 | 8/2003 | Molina et al. |
| 6,612,992 B1 | 9/2003 | Hossack et al. |
| 6,613,002 B1 | 9/2003 | Clark et al. |
| 6,623,431 B1 | 9/2003 | Sakuma et al. |
| 6,641,538 B2 | 11/2003 | Nakaya et al. |
| 6,647,135 B2 | 11/2003 | Bonnefous |
| 6,687,386 B1 | 2/2004 | Ito et al. |
| 6,749,569 B1 | 6/2004 | Pellegretti |
| 6,754,608 B2 | 6/2004 | Svanerudh et al. |
| 6,755,789 B2 | 6/2004 | Stringer et al. |
| 6,840,379 B2 | 1/2005 | Franks-Farah et al. |
| 6,857,196 B2 | 2/2005 | Dalrymple |
| 6,979,294 B1 | 12/2005 | Selzer et al. |
| 7,074,187 B2 | 7/2006 | Selzer et al. |
| 7,244,234 B2 | 7/2007 | Ridley et al. |
| 7,359,554 B2 | 4/2008 | Klingensmith et al. |
| 7,534,209 B2 | 5/2009 | Abend et al. |
| 7,599,730 B2 | 10/2009 | Hunter et al. |
| 7,637,870 B2 | 12/2009 | Flaherty et al. |
| 7,681,579 B2 | 3/2010 | Schwartz |
| 7,691,061 B2 | 4/2010 | Hirota |
| 7,699,779 B2 | 4/2010 | Sasaki et al. |
| 7,720,520 B2 | 5/2010 | Willis |
| 7,727,153 B2 | 6/2010 | Fritz et al. |
| 7,734,326 B2 | 6/2010 | Pedain et al. |
| 7,831,449 B2 | 11/2010 | Ying et al. |
| 7,905,837 B2 | 3/2011 | Suzuki |
| 7,925,327 B2 | 4/2011 | Weese |
| 7,927,278 B2 | 4/2011 | Selzer et al. |
| 8,014,848 B2 | 9/2011 | Birkenbach et al. |
| 8,050,523 B2 * | 11/2011 | Younge ................ A61B 5/6852 385/13 |
| 8,060,181 B2 | 11/2011 | Rodriguez Ponce et al. |
| 8,068,581 B2 | 11/2011 | Boese et al. |
| 8,075,488 B2 | 12/2011 | Burton |
| 8,090,427 B2 | 1/2012 | Eck et al. |
| 8,105,239 B2 | 1/2012 | Specht |
| 8,172,754 B2 | 5/2012 | Watanabe et al. |
| 8,175,368 B2 | 5/2012 | Sathyanarayana |
| 8,200,313 B1 | 6/2012 | Rambod et al. |
| 8,211,023 B2 | 7/2012 | Swan et al. |
| 8,228,347 B2 | 7/2012 | Beasley et al. |
| 8,298,147 B2 | 10/2012 | Huennekens et al. |
| 8,303,505 B2 | 11/2012 | Webler et al. |
| 8,323,202 B2 | 12/2012 | Roschak et al. |
| 8,328,727 B2 | 12/2012 | Miele et al. |
| 8,388,541 B2 | 3/2013 | Messerly et al. |
| 8,409,103 B2 | 4/2013 | Grunwald et al. |
| 8,449,465 B2 | 5/2013 | Nair et al. |
| 8,553,954 B2 | 10/2013 | Saikia |
| 8,556,815 B2 | 10/2013 | Pelissier et al. |
| 8,585,600 B2 | 11/2013 | Liu et al. |
| 8,622,913 B2 | 1/2014 | Dentinger et al. |
| 8,706,457 B2 | 4/2014 | Hart et al. |
| 8,727,988 B2 | 5/2014 | Flaherty et al. |
| 8,734,357 B2 | 5/2014 | Taylor |
| 8,744,211 B2 | 6/2014 | Owen |
| 8,754,865 B2 | 6/2014 | Merritt et al. |
| 8,764,663 B2 | 7/2014 | Smok et al. |
| 8,781,194 B2 | 7/2014 | Malek et al. |
| 8,781,555 B2 | 7/2014 | Burnside et al. |
| 8,790,263 B2 | 7/2014 | Randall et al. |
| 8,849,382 B2 | 9/2014 | Cox et al. |
| 8,939,908 B2 | 1/2015 | Suzuki et al. |
| 8,961,420 B2 | 2/2015 | Zhang |
| 9,022,940 B2 | 5/2015 | Meier |
| 9,138,290 B2 | 9/2015 | Hadjicostis |
| 9,155,517 B2 | 10/2015 | Dunbar et al. |
| 9,204,858 B2 | 12/2015 | Pelissier et al. |
| 9,220,477 B2 | 12/2015 | Urabe et al. |
| 9,257,220 B2 | 2/2016 | Nicholls et al. |
| 9,295,447 B2 | 3/2016 | Shah |
| 9,320,493 B2 | 4/2016 | Visveshwara |
| 9,357,980 B2 | 6/2016 | Toji et al. |
| 9,364,171 B2 | 6/2016 | Harris et al. |
| 9,427,207 B2 | 8/2016 | Sheldon et al. |
| 9,445,780 B2 | 9/2016 | Hossack et al. |
| 9,456,766 B2 | 10/2016 | Cox et al. |
| 9,456,804 B2 | 10/2016 | Tamada |
| 9,459,087 B2 | 10/2016 | Dunbar et al. |
| 9,468,413 B2 | 10/2016 | Hall et al. |
| 9,492,097 B2 | 11/2016 | Wilkes et al. |
| 9,521,961 B2 | 12/2016 | Silverstein et al. |
| 9,554,716 B2 | 1/2017 | Burnside et al. |
| 9,582,876 B2 | 2/2017 | Specht |
| 9,597,008 B2 | 3/2017 | Henkel et al. |
| 9,610,061 B2 | 4/2017 | Ebbini et al. |
| 9,636,031 B2 | 5/2017 | Cox |
| 9,649,037 B2 | 5/2017 | Lowe et al. |
| 9,649,048 B2 | 5/2017 | Cox et al. |
| 9,702,969 B2 | 7/2017 | Hope Simpson et al. |
| 9,715,757 B2 | 7/2017 | Ng et al. |
| 9,717,415 B2 | 8/2017 | Cohen et al. |
| 9,731,066 B2 | 8/2017 | Liu et al. |
| 9,814,433 B2 | 11/2017 | Benishti et al. |
| 9,814,531 B2 | 11/2017 | Yagi et al. |
| 9,861,337 B2 | 1/2018 | Patwardhan et al. |
| 9,895,138 B2 | 2/2018 | Sasaki |
| 9,913,605 B2 | 3/2018 | Harris et al. |
| 9,949,720 B2 | 4/2018 | Southard et al. |
| 10,043,272 B2 | 8/2018 | Forzoni et al. |
| 10,380,919 B2 | 8/2019 | Savitsky et al. |
| 10,380,920 B2 | 8/2019 | Savitsky et al. |
| 10,424,225 B2 | 9/2019 | Nataneli et al. |
| 10,434,278 B2 | 10/2019 | Dunbar et al. |
| 10,449,330 B2 | 10/2019 | Newman et al. |

(56) References Cited

U.S. PATENT DOCUMENTS

| | | |
|---|---|---|
| 10,524,691 B2 | 1/2020 | Newman et al. |
| 10,674,935 B2 | 6/2020 | Henkel et al. |
| 10,751,509 B2 | 8/2020 | Misener |
| 10,758,155 B2 | 9/2020 | Henkel et al. |
| 10,765,343 B2 | 9/2020 | Henkel et al. |
| 10,896,628 B2 | 1/2021 | Savitsky et al. |
| 11,062,624 B2 | 7/2021 | Savitsky et al. |
| 11,120,709 B2 | 9/2021 | Savitsky et al. |
| 11,311,269 B2 | 4/2022 | Dunbar et al. |
| 11,315,439 B2 | 4/2022 | Savitsky et al. |
| 11,600,201 B1 | 3/2023 | Savitsky et al. |
| 2002/0038088 A1 | 3/2002 | Imran et al. |
| 2002/0148277 A1 | 10/2002 | Umeda |
| 2003/0047126 A1 | 3/2003 | Tomaschko |
| 2003/0060714 A1 | 3/2003 | Henderson et al. |
| 2003/0073900 A1 | 4/2003 | Senarith et al. |
| 2003/0093001 A1 | 5/2003 | Martikainen |
| 2003/0106825 A1 | 6/2003 | Molina et al. |
| 2003/0120154 A1 | 6/2003 | Sauer et al. |
| 2004/0055925 A1 | 3/2004 | Franks-Farah et al. |
| 2005/0000975 A1 | 1/2005 | Carco et al. |
| 2005/0049504 A1 | 3/2005 | Lo et al. |
| 2005/0165299 A1 | 7/2005 | Kressy et al. |
| 2005/0251030 A1 | 11/2005 | Azar et al. |
| 2005/0267365 A1 | 12/2005 | Sokulin et al. |
| 2006/0013523 A1 | 1/2006 | Childlers et al. |
| 2006/0015039 A1 | 1/2006 | Cassidy et al. |
| 2006/0020204 A1 | 1/2006 | Serra et al. |
| 2006/0079781 A1 | 4/2006 | Germond-Rouet et al. |
| 2006/0184029 A1 | 8/2006 | Haim et al. |
| 2006/0210130 A1 | 9/2006 | Germond-Rouet et al. |
| 2007/0043341 A1 | 2/2007 | Anderson et al. |
| 2007/0049822 A1 | 3/2007 | Bunce et al. |
| 2007/0073155 A1 | 3/2007 | Park et al. |
| 2007/0199848 A1 | 8/2007 | Ellswood et al. |
| 2007/0239120 A1 | 10/2007 | Brock et al. |
| 2007/0249911 A1 | 10/2007 | Simon |
| 2008/0021322 A1 | 1/2008 | Stone et al. |
| 2008/0033293 A1 | 2/2008 | Beasley et al. |
| 2008/0033759 A1 | 2/2008 | Finlay |
| 2008/0051657 A1 | 2/2008 | Rold |
| 2008/0146915 A1 | 6/2008 | McMorrow |
| 2008/0177186 A1 | 7/2008 | Slater et al. |
| 2008/0221425 A1 | 9/2008 | Olson et al. |
| 2008/0294037 A1 | 11/2008 | Richter |
| 2008/0300491 A1 | 12/2008 | Bonde et al. |
| 2009/0012399 A1 | 1/2009 | Sunagawa et al. |
| 2009/0143672 A1 | 6/2009 | Harms et al. |
| 2009/0143684 A1 | 6/2009 | Cermak et al. |
| 2009/0156926 A1 | 6/2009 | Messerly et al. |
| 2009/0306509 A1 | 12/2009 | Pedersen et al. |
| 2010/0020926 A1 | 1/2010 | Boese et al. |
| 2010/0106015 A1 | 4/2010 | Norris |
| 2010/0179428 A1 | 7/2010 | Pedersen et al. |
| 2010/0211026 A2 | 8/2010 | Sheetz et al. |
| 2010/0277305 A1 | 11/2010 | Garner et al. |
| 2010/0286515 A1 | 11/2010 | Gravenstein et al. |
| 2010/0312121 A1 | 12/2010 | Guan |
| 2011/0002518 A1 | 1/2011 | Ziv-Ari et al. |
| 2011/0071404 A1 | 3/2011 | Schmitt et al. |
| 2011/0166451 A1 | 7/2011 | Blaivas et al. |
| 2011/0288405 A1 | 11/2011 | Razavi et al. |
| 2011/0295108 A1 | 12/2011 | Cox et al. |
| 2011/0313293 A1 | 12/2011 | Lindekugel et al. |
| 2012/0136242 A1 | 5/2012 | Qi et al. |
| 2012/0179038 A1 | 7/2012 | Meurer et al. |
| 2012/0197132 A1 | 8/2012 | O'Connor |
| 2012/0209121 A1 | 8/2012 | Boudier |
| 2012/0220865 A1 | 8/2012 | Brown et al. |
| 2012/0238875 A1 | 9/2012 | Savitsky et al. |
| 2012/0277576 A1 | 11/2012 | Lui |
| 2013/0041250 A1 | 2/2013 | Pelissier et al. |
| 2013/0102889 A1 | 4/2013 | Southard et al. |
| 2013/0131499 A1 | 5/2013 | Chan et al. |
| 2013/0131502 A1 | 5/2013 | Blaivas et al. |
| 2013/0150724 A1 | 6/2013 | Blaivas et al. |
| 2013/0188832 A1 | 7/2013 | Ma et al. |
| 2013/0218024 A1 | 8/2013 | Boctor et al. |
| 2013/0324840 A1 | 12/2013 | Zhongping et al. |
| 2014/0005530 A1 | 1/2014 | Liu et al. |
| 2014/0031690 A1 | 1/2014 | Toji et al. |
| 2014/0036091 A1* | 2/2014 | Zalev .................. A61B 8/4444 |
| | | 348/163 |
| 2014/0073976 A1 | 3/2014 | Fonte et al. |
| 2014/0100440 A1 | 4/2014 | Cheline et al. |
| 2014/0155737 A1 | 6/2014 | Manzke et al. |
| 2014/0180098 A1 | 6/2014 | Flaherty et al. |
| 2014/0188133 A1 | 7/2014 | Misener |
| 2014/0188440 A1 | 7/2014 | Donhowe et al. |
| 2014/0257104 A1 | 9/2014 | Dunbar et al. |
| 2014/0276059 A1 | 9/2014 | Sheehan |
| 2014/0276081 A1 | 9/2014 | Tegels |
| 2014/0276085 A1 | 9/2014 | Miller |
| 2014/0276690 A1 | 9/2014 | Grace |
| 2014/0343431 A1 | 11/2014 | Vajinepalli et al. |
| 2015/0005738 A1 | 1/2015 | Blacker |
| 2015/0011887 A1 | 1/2015 | Ahn et al. |
| 2015/0065916 A1 | 3/2015 | Maguire et al. |
| 2015/0073279 A1 | 3/2015 | Cai et al. |
| 2015/0112200 A1 | 4/2015 | Oberg et al. |
| 2015/0209113 A1 | 7/2015 | Burkholz et al. |
| 2015/0209526 A1 | 7/2015 | Matsubara et al. |
| 2015/0294497 A1 | 10/2015 | Ng et al. |
| 2015/0297097 A1 | 10/2015 | Matsubara et al. |
| 2015/0327841 A1 | 11/2015 | Banjanin et al. |
| 2015/0359991 A1 | 12/2015 | Dunbar et al. |
| 2016/0029995 A1 | 2/2016 | Navratil et al. |
| 2016/0029998 A1* | 2/2016 | Brister .................. A61B 8/0833 |
| | | 600/424 |
| 2016/0058420 A1 | 3/2016 | Cinthio et al. |
| 2016/0100970 A1 | 4/2016 | Brister et al. |
| 2016/0101263 A1* | 4/2016 | Blumenkranz ....... A61B 5/1076 |
| | | 600/117 |
| 2016/0113699 A1 | 4/2016 | Sverdlik et al. |
| 2016/0120607 A1 | 5/2016 | Sorotzkin et al. |
| 2016/0143622 A1 | 5/2016 | Xie et al. |
| 2016/0166232 A1 | 6/2016 | Merritt |
| 2016/0202053 A1 | 7/2016 | Walker et al. |
| 2016/0213398 A1 | 7/2016 | Liu |
| 2016/0278743 A1 | 9/2016 | Kawashima |
| 2016/0278869 A1 | 9/2016 | Grunwald |
| 2016/0296208 A1 | 10/2016 | Sethuraman et al. |
| 2016/0374644 A1 | 12/2016 | Mauldin, Jr. et al. |
| 2017/0079548 A1 | 3/2017 | Silverstein et al. |
| 2017/0086785 A1 | 3/2017 | Bjaerum |
| 2017/0100092 A1 | 4/2017 | Kruse et al. |
| 2017/0164923 A1 | 6/2017 | Matsumoto |
| 2017/0172424 A1 | 6/2017 | Eggers et al. |
| 2017/0188839 A1 | 7/2017 | Tashiro |
| 2017/0196535 A1 | 7/2017 | Arai et al. |
| 2017/0215842 A1 | 8/2017 | Ryu et al. |
| 2017/0259013 A1 | 9/2017 | Boyden et al. |
| 2017/0265840 A1 | 9/2017 | Bharat et al. |
| 2017/0303894 A1 | 10/2017 | Scully |
| 2017/0367678 A1 | 12/2017 | Sirtori et al. |
| 2018/0015256 A1 | 1/2018 | Southard et al. |
| 2018/0116723 A1 | 5/2018 | Hettrick et al. |
| 2018/0125450 A1 | 5/2018 | Blackbourne et al. |
| 2018/0161502 A1 | 6/2018 | Nanan et al. |
| 2018/0199914 A1 | 7/2018 | Ramachandran et al. |
| 2018/0214119 A1 | 8/2018 | Mehrmohammadi et al. |
| 2018/0225993 A1 | 8/2018 | Buras et al. |
| 2018/0228465 A1 | 8/2018 | Southard et al. |
| 2018/0235576 A1 | 8/2018 | Brannan |
| 2018/0250078 A1 | 9/2018 | Shochat et al. |
| 2018/0272108 A1* | 9/2018 | Padilla ................ A61M 25/005 |
| 2018/0279096 A1 | 10/2018 | Cox et al. |
| 2018/0286287 A1 | 10/2018 | Razzaque |
| 2018/0310955 A1 | 11/2018 | Lindekugel et al. |
| 2018/0317881 A1 | 11/2018 | Astigarraga et al. |
| 2018/0366035 A1 | 12/2018 | Dunbar et al. |
| 2019/0060014 A1 | 2/2019 | Hazelton et al. |
| 2019/0069923 A1 | 3/2019 | Wang |
| 2019/0076121 A1 | 3/2019 | Southard et al. |

(56) References Cited

U.S. PATENT DOCUMENTS

| | | |
|---|---|---|
| 2019/0088019 A1 | 3/2019 | Prevrhal et al. |
| 2019/0105017 A1 | 4/2019 | Hastings |
| 2019/0117190 A1 | 4/2019 | Djajadiningrat et al. |
| 2019/0223757 A1 | 7/2019 | Durfee |
| 2019/0239850 A1 | 8/2019 | Dalvin et al. |
| 2019/0282324 A1 | 9/2019 | Freeman et al. |
| 2019/0298457 A1 | 10/2019 | Bharat |
| 2019/0307516 A1 | 10/2019 | Schotzko et al. |
| 2019/0339525 A1 | 11/2019 | Yanof et al. |
| 2019/0355278 A1 | 11/2019 | Sainsbury et al. |
| 2019/0365348 A1 | 12/2019 | Toume et al. |
| 2020/0041261 A1 | 2/2020 | Bernstein et al. |
| 2020/0069285 A1 | 3/2020 | Annangi et al. |
| 2020/0069929 A1 | 3/2020 | Mason et al. |
| 2020/0113540 A1 | 4/2020 | Gijsbers et al. |
| 2020/0129136 A1 | 4/2020 | Harding et al. |
| 2020/0188028 A1 | 6/2020 | Feiner et al. |
| 2020/0230391 A1 | 7/2020 | Burkholz et al. |
| 2021/0007710 A1 | 1/2021 | Douglas |
| 2021/0045716 A1* | 2/2021 | Shiran .................... G06T 7/246 |
| 2021/0166583 A1 | 6/2021 | Buras et al. |
| 2021/0307838 A1 | 10/2021 | Xia et al. |
| 2021/0353255 A1 | 11/2021 | Schneider et al. |
| 2021/0402144 A1 | 12/2021 | Messerly |
| 2022/0022969 A1 | 1/2022 | Misener |
| 2022/0031965 A1 | 2/2022 | Durfee |
| 2022/0039685 A1 | 2/2022 | Misener et al. |
| 2022/0039777 A1 | 2/2022 | Durfee |
| 2022/0096797 A1 | 3/2022 | Prince |
| 2022/0104886 A1 | 4/2022 | Blanchard et al. |
| 2022/0160434 A1 | 5/2022 | Messerly et al. |
| 2022/0168050 A1 | 6/2022 | Sowards et al. |
| 2022/0172354 A1 | 6/2022 | Misener et al. |
| 2022/0211442 A1 | 7/2022 | McLaughlin et al. |
| 2022/0381630 A1 | 12/2022 | Sowards et al. |
| 2023/0113291 A1 | 4/2023 | de Wild et al. |
| 2023/0240643 A1 | 8/2023 | Cermak et al. |
| 2023/0389893 A1 | 12/2023 | Misener et al. |
| 2024/0008929 A1 | 1/2024 | Misener et al. |
| 2024/0050061 A1 | 2/2024 | McLaughlin et al. |
| 2024/0058074 A1 | 2/2024 | Misener |
| 2024/0062678 A1 | 2/2024 | Sowards et al. |

FOREIGN PATENT DOCUMENTS

| | | |
|---|---|---|
| EP | 0933063 A1 | 8/1999 |
| EP | 1504713 A1 | 2/2005 |
| EP | 1591074 B1 | 5/2008 |
| EP | 3181083 A1 | 6/2017 |
| EP | 3530221 A1 | 8/2019 |
| JP | 2000271136 A | 10/2000 |
| JP | 2014150928 A | 8/2014 |
| JP | 2018175547 A | 11/2018 |
| KR | 20180070878 A | 6/2018 |
| KR | 20190013133 A | 2/2019 |
| WO | 2013059714 A1 | 4/2013 |
| WO | 2014/115150 A1 | 7/2014 |
| WO | WO2014174305 * | 10/2014 |
| WO | 2015/017270 A1 | 2/2015 |
| WO | 2017096487 A1 | 6/2017 |
| WO | 2017214428 A1 | 12/2017 |
| WO | 2018/026878 A1 | 2/2018 |
| WO | 2018134726 A1 | 7/2018 |
| WO | WO2018206473 * | 11/2018 |
| WO | 2019/232451 A1 | 12/2019 |
| WO | 2020/002620 A1 | 1/2020 |
| WO | 2020/016018 A1 | 1/2020 |
| WO | 2019/232454 A9 | 2/2020 |
| WO | 2020/044769 A1 | 3/2020 |
| WO | 2020102665 | 5/2020 |
| WO | 2020/186198 A1 | 9/2020 |
| WO | 2022/031762 A1 | 2/2022 |
| WO | 2022/072727 A2 | 4/2022 |
| WO | 2022/081904 A1 | 4/2022 |
| WO | 2022-203713 A2 | 9/2022 |
| WO | 2022263763 A1 | 12/2022 |
| WO | 2023235435 A1 | 12/2023 |
| WO | 2024010940 A1 | 1/2024 |
| WO | 2024039608 A1 | 2/2024 |
| WO | 2024039719 A1 | 2/2024 |

OTHER PUBLICATIONS

Pagoulatos, N. et al. "New spatial localizer based on fiber optics with applications in 3D ultrasound imaging" Proceeding of Spie, vol. 3976 (Apr. 18, 2000; Apr. 18, 2000).

PCT/US2021/042369 filed Jul. 20, 2021 International Search Report and Written Opinion dated Oct. 25, 2021.

PCT/US2021/044419 filed Aug. 3, 2021 International Search Report and Written Opinion dated Nov. 19, 2021.

PCT/US2021/055076 filed Oct. 14, 2021 International Search Report and Written Opinion dated Mar. 25, 2022.

U.S. Appl. No. 17/397,486, filed Aug. 9, 2021 Restriction Requirement dated Aug. 12, 2022.

Lu Zhenyu et al "Recent advances in 5 robot-assisted echography combining perception control and cognition." Cognitive Computation and Systems the Institution of Engineering and Technology, Michael Faraday House, Six Hills Way, Stevenage Herts. SG1 2AY UK vol. 2 No. 3 Sep. 2, 2020 (Sep. 2, 2020).

PCT/US2021/045218 filed Aug. 9, 2021 International Search Report and Written Opinion dated Nov. 23, 2021.

PCT/US2021/049123 filed Sep. 3, 2021 International Search Report and Written Opinion dated May 16, 2022.

PCT/US2021/053018 filed Sep. 30, 2021 International Search Report and Written Opinion dated May 3, 2022.

PCT/US2021/060622 filed Nov. 23, 2021 International Search Report and Written Opinion dated Mar. 3, 2022.

PCT/US2021/061267 filed Nov. 30, 2021 International Search Report and Written Opinion dated Mar. 9, 2022.

PCT/US2021/061276 filed Nov. 30, 2021 International Search Report and Written Opinion dated Mar. 9, 2022.

Sebastian Vogt: "Real-Time Augmented Reality for Image-Guided Interventions", Oct. 5, 2009, XPO55354720, Retrieved from the Internet: URL: https://opus4.kobv.de/opus4-fau/frontdoor/deliver/index/docId/1235/file/SebastianVogtDissertation.pdf.

U.S. Appl. No. 15/951,903, filed Apr. 12, 2018 Board Decision dated Apr. 20, 2022.

U.S. Appl. No. 15/951,903, filed Apr. 12, 2018 Notice of Allowance dated May 2, 2022.

William F Garrett et al: "Real-time incremental visualization of dynamic ultrasound volumes using parallel BSP trees", Visualization '96. Proceedings, IEEE, NE, Oct. 27, 1996, pp. 235-ff, XPO58399771, ISBN: 978-0-89791-864-0 abstract, figures 1-7, pp. 236-240.

Ezono, eZSimulator, https://www.ezono.com/en/ezsimulator/, last accessed Sep. 13, 2022.

PCT/US2021/050973 filed Sep. 17, 2021 International Search Report and Written Opinion dated Nov. 7, 2022.

Sonosim, https://sonosim.com/ultrasound-simulation/? last accessed Sep. 13, 2022.

U.S. Appl. No. 17/380,767, filed Jul. 20, 2021 Non-Final Office Action dated Mar. 6, 2023.

U.S. Appl. No. 17/380,767, filed Jul. 20, 2021 Restriction Requirement dated Dec. 15, 2022.

U.S. Appl. No. 17/393,283, filed Aug. 3, 2021 Non-Final Office Action dated Mar. 31, 2023.

U.S. Appl. No. 17/393,283, filed Aug. 3, 2021 Restriction Requirement dated Jan. 12, 2023.

U.S. Appl. No. 17/397,486, filed Aug. 9, 2021 Non-Final Office Action dated Jan. 23, 2023.

U.S. Appl. No. 17/491,308, filed Sep. 30, 2021 Restriction Requirement dated Feb. 27, 2023.

PCT/US12/61182 International Seach Report and Written Opinion dated Mar. 11, 2013.

PCT/US2021/049123 filed Sep. 3, 2021 International Search Report and Written Opinion dated Feb. 4, 2022.

(56) References Cited

OTHER PUBLICATIONS

PCT/US2021/049294 filed Sep. 7, 2021 International Search Report and Written Opinion dated Dec. 8, 2021.
PCT/US2021/049712 filed Sep. 9, 2021 International Search Report and Written Opinion dated Dec. 14, 2021.
PCT/US2021/052055 filed Sep. 24, 2021 International Search Report and Written Opinion dated Dec. 20, 2021.
U.S. Appl. No. 13/656,563, filed Oct. 19, 2012 Decision on Appeal dated Nov. 1, 2017.
U.S. Appl. No. 13/656,563, filed Oct. 19, 2012 Examiner's Answer dated Nov. 16, 2015.
U.S. Appl. No. 13/656,563, filed Oct. 19, 2012 Final Office Action dated Dec. 5, 2014.
U.S. Appl. No. 13/656,563, filed Oct. 19, 2012 Non-Final Office Action dated Jul. 18, 2014.
U.S. Appl. No. 15/650,474, filed Jul. 14, 2017 Final Office Action dated Jun. 2, 2020.
U.S. Appl. No. 15/650,474, filed Jul. 14, 2017 Non-Final Office Action dated Dec. 16, 2019.
U.S. Appl. No. 15/650,474, filed Jul. 14, 2017 Notice of Allowance dated Dec. 11, 2020.
U.S. Appl. No. 15/650,474, filed Jul. 14, 2017 Notice of Allowance dated Mar. 1, 2021.
U.S. Appl. No. 15/951,903, filed Apr. 12, 2018 Advisory Action dated Dec. 22, 2020.
U.S. Appl. No. 15/951,903, filed Apr. 12, 2018 Examiner's Answer dated Jun. 3, 2021.
U.S. Appl. No. 15/951,903, filed Apr. 12, 2018 Final Office Action dated Oct. 13, 2020.
U.S. Appl. No. 15/951,903, filed Apr. 12, 2018 Non-Final Office Action dated May 22, 2020.
U.S. Appl. No. 17/020,476, filed Sep. 14, 2020 Non-Final Office Action dated Feb. 9, 2022.
State, A., et al. (Aug. 1996). Technologies for augmented reality systems: Realizing ultrasound-guided needle biopsies. In Proceedings of the 23rd annual conference on computer graphics and interactive techniques (pp. 439-446) (Year: 1996).
Stolka, P.J., et al., (2014). Needle Guidance Using Handheld Stereo Vision and Projection for Ultrasound-Based Interventions. In: Galland, P., Hata, N., Barillot, C., Hornegger, J., Howe, R. (eds) Medical Image Computing and Computer-Assisted Intervention—MICCAI 2014. MICCAI 2014. (Year: 2014).
U.S. Appl. No. 17/397,486, filed Aug. 9, 2021 Final Office Action dated Aug. 4, 2023.
U.S. Appl. No. 17/491,308, filed Sep. 30, 2021 Final Office Action dated Aug. 29, 2023.
U.S. Appl. No. 17/491,308, filed Sep. 30, 2021 Non-Final Office Action dated Jun. 5, 2023.
U.S. Appl. No. 17/832,389, filed Jun. 3, 2022 Restriction Requirement dated Jul. 13, 2023.
PCT/US2023/024067 filed May 31, 2023 International Search Report and Written Opinion dated Sep. 15, 2023.
PCT/US2023/027147 filed Jul. 7, 2023 International Search Report and Written Opinion dated Oct. 2, 2023.
PCT/US2023/030160 filed Aug. 14, 2023 International Search Report and Written Opinion dated Oct. 23, 2023.
PCT/US2023/030347 filed Aug. 16, 2023 International Search Report and Written Opinion dated Nov. 6, 2023.
Practical guide for safe central venous catheterization and management 2017 Journal of Anesthesia vol. 34 published online Nov. 30, 2019 pp. 167-186.
U.S. Appl. No. 17/380,767, filed Jul. 20, 2021 Notice of Allowance dated Aug. 31, 2023.
U.S. Appl. No. 17/393,283, filed Aug. 3, 2021 Final Office Action dated Oct. 16, 2023.
U.S. Appl. No. 17/397,486, filed Aug. 9, 2021 Advisory Action dated Oct. 5, 2023.
U.S. Appl. No. 17/491,308, filed Sep. 30, 2021 Board Decison dated Oct. 25, 2023.
U.S. Appl. No. 17/832,389, filed Jun. 3, 2022 Non-Final Office Action dated Oct. 6, 2023.
U.S. Appl. No. 17/861,031, filed Jul. 8, 2022 Non-Final Office Action dated Sep. 14, 2023.
U.S. Appl. No. 17/393,283, filed Aug. 3, 2021 Advisory Action dated Jan. 19, 2024.
U.S. Appl. No. 17/478,754, filed Sep. 17, 2021 Restriction Requirement dated Jan. 22, 2024.
U.S. Appl. No. 17/832,389, filed Jun. 3, 2022 Final Office Action dated Jan. 25, 2024.
U.S. Appl. No. 17/393,283, filed Aug. 3, 2021 Non-Final Office Action dated Feb. 29, 2024.
U.S. Appl. No. 17/397,486, filed Aug. 9, 2021 Non-Final Office Action dated Mar. 1, 2024.
U.S. Appl. No. 17/397,486, filed Aug. 9, 2021 Notice of Allowance dated Jul. 10, 2024.
U.S. Appl. No. 17/478,754, filed Sep. 17, 2021 Non-Final Office Action dated Jul. 1, 2024.
U.S. Appl. No. 17/491,308, filed Sep. 30, 2021 Non-Final Office Action dated Mar. 22, 2024.
U.S. Appl. No. 17/491,308, filed Sep. 30, 2021 Notice of Allowance dated Jun. 27, 2024.
U.S. Appl. No. 17/832,389, filed Jun. 3, 2022 Advisory Action dated Apr. 4, 2024.
U.S. Appl. No. 17/832,389, filed Jun. 3, 2022 Notice of Allowance dated May 15, 2024.
U.S. Appl. No. 17/861,031, filed Jul. 8, 2022 Advisory Action dated Jun. 7, 2024.
U.S. Appl. No. 17/861,031, filed Jul. 8, 2022 Final Office Action dated Mar. 15, 2024.
U.S. Appl. No. 17/861,031, filed Jul. 8, 2022 Notice of Allowance dated Jul. 3, 2024.
U.S. Appl. No. 17/393,283, filed Aug. 3, 2021 Notice of Allowance dated Sep. 18, 2024.
U.S. Appl. No. 17/888,359, filed Aug. 15, 2022 Restriction Requirement dated Sep. 5, 2024.
U.S. Appl. No. 18/385,101, filed Oct. 30, 2023 Notice of Allowance dated Aug. 20, 2024.

* cited by examiner

ULTRASOUND IMAGING SYSTEM FOR GENERATION OF A THREE-DIMENSIONAL ULTRASOUND IMAGE

PRIORITY

This application claims the benefit of priority to U.S. Provisional Application No. 63/092,368, filed Oct. 15, 2020, which is incorporated by reference in its entirety into this application.

BACKGROUND

When using ultrasound imaging systems to place medical devices, it is important to maintain a field of view of the target area. If the field of view of the target area is not maintained due to movement of the probe, it can be tedious and consuming to attempt to reorient the ultrasound probe to maintain the field of view. Furthermore, it would be beneficial to the clinician and the patient if information from the ultrasound probe could be used to generate a three-dimensional ultrasound image of the target area, to assist with medical device placement. Disclosed herein is an ultrasound imaging system and method of use that address the foregoing.

SUMMARY

Disclosed herein is an ultrasound imaging system configured to generate a 3D ultrasound image of a target area including a console including one or more processors and non-transitory computer readable medium having stored thereon one or more logic modules. In some embodiments, the one or more logic modules may be configured to detect a point of reference wherein the point of reference is one or more anatomical targets, a reference magnet configured to generate a magnetic field over the target area, or an elongate medical device. The ultrasound imaging system further includes an ultrasound probe configured to acquire a plurality of ultrasound images of the target area. In some embodiments the ultrasound probe may be coupled to the console by an ultrasound probe connector having optical fiber including one or more core fibers. In some embodiments, the probe may have one or more electromagnetic sensors configured to detect a magnetic field and one or more accelerometers configured to detect acceleration of the probe. The console may be configured to generate three-dimensional visualization by stitching together the plurality of ultrasound images, starting from the point of reference. In some embodiments, the point of reference may include the ultrasound probe, the reference magnet, the one or more anatomical targets, or the elongate medical device.

In some embodiments, the one or more core fibers include a plurality of sensors distributed along a longitudinal length of a corresponding core fiber and each sensor of the plurality of sensors is configured to reflect a light signal of a different spectral width based on received incident light, and change a characteristic of the reflected light signal for use in determining a physical state of the optical fiber.

In some embodiments, the optical fiber is a single-core optical fiber and wherein an incident light is provided in pulses.

In some embodiments, the optical fiber is a multi-core optical fiber including a plurality of core fibers, and wherein an incident light propagates along a first core fiber and the reflect light signal propagates along a second core fiber.

In some embodiments, the one or more logic modules, when executed by the one or more processors, may cause operations including determining the shape of the one or more core fibers, transmitting and receiving optical signals, determining ultrasound probe movement, associating ultrasound probe movement with ultrasound images, and compiling a 3D ultrasound image.

In some embodiments, determining ultrasound probe movement includes using the shape of the one or more core fibers taken in relation to the ultrasound probe.

In some embodiments, determining the shape of the one or more core fibers includes using the transmitted and received optical signals.

In some embodiments, associating ultrasound probe movement with ultrasound images includes associating ultrasound images with the shape of the one or more core fibers taken in relation to the ultrasound probe.

In some embodiments, compiling a 3D ultrasound image includes using ultrasound images associated with the shape of the one or more core fibers taken in relation to the point of reference.

In some embodiments, the one or more logic modules, when executed by the one or more processors, may cause operations including detecting and selecting one or more anatomical targets as the point of reference, determining ultrasound probe movement, in relation to the one or more anatomical targets, associating ultrasound probe movement with ultrasound images, and compiling a 3D ultrasound image.

In some embodiments, the one or more anatomical targets are selected from a group consisting of a bone, a vein, an artery, a muscle, a tendon, a ligament, a nerve and a joint.

In some embodiments, associating ultrasound probe movement with ultrasound images includes associating ultrasound images with the one or more anatomical targets as the point of reference.

In some embodiments, compiling a 3D ultrasound image includes using ultrasound images associated with one or more anatomical targets as the point of reference.

In some embodiments, the one or more logic modules, when executed by the one or more processors, may cause operations including determining ultrasound probe movement, in relation to the elongate medical device, associating ultrasound probe movement with ultrasound images, and compiling a 3D ultrasound image.

In some embodiments, the elongate medical device is selected from the group consisting of a catheter, a stylet, a needle and a guidewire.

In some embodiments, associating ultrasound probe movement with ultrasound images includes associating ultrasound images with the elongate medical device as the point of reference.

In some embodiments, compiling a 3D ultrasound image includes using ultrasound images associated with the elongate medical device as the point of reference.

In some embodiments, the one or more logic modules, when executed by the one or more processors, may cause operations including detecting measured magnetic field strength values, detecting measured probe acceleration values, determining ultrasound probe movement, in relation to the reference magnet, associating ultrasound probe movement with ultrasound images, and compiling a 3D ultrasound image.

In some embodiments, determining ultrasound probe movement includes using detected magnetic field strength values in relation to the reference magnet.

In some embodiments, determining ultrasound probe movement includes using measured probe acceleration values detected by the one or more accelerometers.

In some embodiments, associating ultrasound probe movement with ultrasound images includes associating ultrasound images with measured magnetic field strength values.

In some embodiments, associating ultrasound probe movement with ultrasound images includes associating ultrasound images with measured probe acceleration values.

In some embodiments, compiling a 3D ultrasound image includes using ultrasound images associated with measured magnetic field strength values in relation to the reference magnet.

In some embodiments, compiling a 3D ultrasound image includes using ultrasound images associated with measured probe acceleration values.

Also disclosed herein is a method of using an ultrasound imaging system to create a 3D ultrasound image of a target area including determining a point of reference in the target area using one or more of a reference magnet and one or more electromagnetic sensors, one or more accelerometers, one or more anatomical targets, an ultrasound probe or an elongate medical device, imaging a target area using the ultrasound probe, having one or more electromagnetic sensors or one or more accelerometers, coupled to a console by an ultrasound probe connector having optical fiber therein, including one or more core fibers, tracking one or more of the ultrasound probe and the elongate medical device, associating ultrasound images with ultrasound probe movement, providing feedback to a user to maintain ultrasound probe alignment with the target area, and compiling a 3D ultrasound image of the target area using the console, the console having one or more processors and non-transitory computer readable medium having stored thereon one or more logic modules.

In some embodiments, the elongate medical device is selected from a group consisting of a catheter, a stylet, a needle and a guidewire.

In some embodiments, compiling a 3D ultrasound image including using detected magnetic field strength values associated with ultrasound images.

In some embodiments, compiling a 3D ultrasound image includes using ultrasound images associated with the shape of the one or more core fibers in relation to the point of reference.

In some embodiments, compiling a 3D ultrasound image includes compiling a 3D image of the path of the elongate medical device.

In some embodiments, providing feedback to a user to maintain ultrasound probe alignment including using the one or more accelerometers to maintain ultrasound probe alignment.

In some embodiments, providing feedback to a user to maintain ultrasound probe alignment including using the one or more anatomical targets to maintain ultrasound probe alignment.

In some embodiments, providing feedback to the user to maintain ultrasound probe alignment includes indicating ultrasound probe tilt, ultrasound probe drift or ultrasound probe twist.

In some embodiments, providing feedback to the user to maintain ultrasound probe alignment includes indicating tissue compression, tissue decompression, or the location of the identified anatomical targets.

In some embodiments, compiling a 3D ultrasound image includes displaying additional elongate medical device purchase prediction and elongate medical device purchase confirmation.

In some embodiments, the additional elongate medical device is a catheter.

In some embodiments, compiling a 3D ultrasound image includes depicting the 3D ultrasound image on the display.

These and other features of the concepts provided herein will become more apparent to those of skill in the art in view of the accompanying drawings and following description, which describe particular embodiments of such concepts in greater detail.

DRAWINGS

A more particular description of the present disclosure will be rendered by reference to specific embodiments thereof that are illustrated in the appended drawings. It is appreciated that these drawings depict only typical embodiments of the invention and are therefore not to be considered limiting of its scope. Example embodiments of the invention will be described and explained with additional specificity and detail through the use of the accompanying drawings in which.

DESCRIPTION

Figure 1:
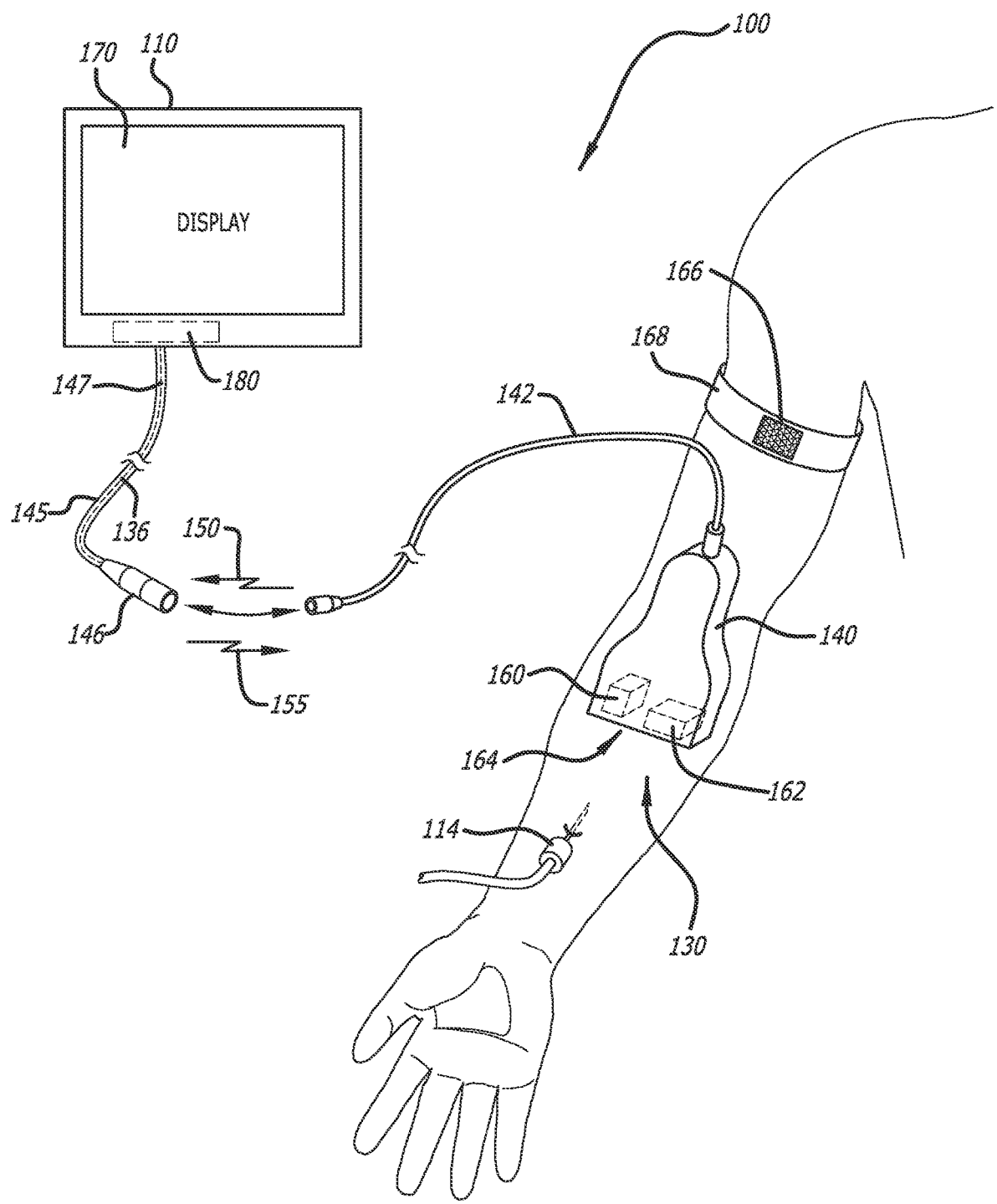
FIG. 1 illustrates a side view of an ultrasound imaging system, according to some embodiments.

Before some particular embodiments are disclosed in greater detail, it should be understood that the particular embodiments disclosed herein do not limit the scope of the concepts provided herein. It should also be understood that a particular embodiment disclosed herein can have features that can be readily separated from the particular embodiment and optionally combined with or substituted for features of any of a number of other embodiments disclosed herein.

Regarding terms used herein, it should also be understood the terms are for the purpose of describing some particular embodiments, and the terms do not limit the scope of the concepts provided herein. Ordinal numbers (e.g., first, second, third, etc.) are generally used to distinguish or identify different features or steps in a group of features or steps, and do not supply a serial or numerical limitation. For example, "first," "second," and "third" features or steps need not necessarily appear in that order, and the particular embodiments including such features or steps need not necessarily be limited to the three features or steps. Labels such as "left," "right," "top," "bottom," "front," "back," and the like are used for convenience and are not intended to imply, for example, any particular fixed location, orientation, or direction. Instead, such labels are used to reflect, for example, relative location, orientation, or directions. Singular forms of "a," "an," and "the" include plural references unless the context clearly dictates otherwise.

With respect to "proximal," a "proximal portion" or a "proximal-end portion" of, for example, a probe disclosed herein includes a portion of the probe intended to be near a clinician when the probe is used on a patient. Likewise, a "proximal length" of, for example, the probe includes a length of the probe intended to be near the clinician when the probe is used on the patient. A "proximal end" of, for example, the probe includes an end of the probe intended to be near the clinician when the probe is used on the patient. The proximal portion, the proximal-end portion, or the proximal length of the probe can include the proximal end of the probe; however, the proximal portion, the proximal-end portion, or the proximal length of the probe need not include the proximal end of the probe. That is, unless context suggests otherwise, the proximal portion, the proximal-end portion, or the proximal length of the probe is not a terminal portion or terminal length of the probe.

With respect to "distal," a "distal portion" or a "distal-end portion" of, for example, a probe disclosed herein includes a portion of the probe intended to be near or in a patient when the probe is used on the patient. Likewise, a "distal length" of, for example, the probe includes a length of the probe intended to be near or in the patient when the probe is used on the patient. A "distal end" of, for example, the probe includes an end of the probe intended to be near or in the patient when the probe is used on the patient. The distal portion, the distal-end portion, or the distal length of the probe can include the distal end of the probe; however, the distal portion, the distal-end portion, or the distal length of the probe need not include the distal end of the probe. That is, unless context suggests otherwise, the distal portion, the distal-end portion, or the distal length of the probe is not a terminal portion or terminal length of the probe.

The term "logic" may be representative of hardware, firmware or software that is configured to perform one or more functions. As hardware, the term logic may refer to or include circuitry having data processing and/or storage functionality. Examples of such circuitry may include, but are not limited or restricted to a hardware processor (e.g., microprocessor, one or more processor cores, a digital signal processor, a programmable gate array, a microcontroller, an application specific integrated circuit "ASIC", etc.), a semiconductor memory, or combinatorial elements.

Additionally, or in the alternative, the term logic may refer to or include software such as one or more processes, one or more instances, Application Programming Interface(s) (API), subroutine(s), function(s), applet(s), servlet(s), routine(s), source code, object code, shared library/dynamic link library (dll), or even one or more instructions. This software may be stored in any type of a suitable non-transitory storage medium, or transitory storage medium (e.g., electrical, optical, acoustical or other form of propagated signals such as carrier waves, infrared signals, or digital signals). Examples of a non-transitory storage medium may include, but are not limited or restricted to a programmable circuit; non-persistent storage such as volatile memory (e.g., any type of random access memory "RAM"); or persistent storage such as non-volatile memory (e.g., read-only memory "ROM", power-backed RAM, flash memory, phase-change memory, etc.), a solid-state drive, hard disk drive, an optical disc drive, or a portable memory device. As firmware, the logic may be stored in persistent storage.

Unless defined otherwise, all technical and scientific terms used herein have the same meaning as commonly understood by those of ordinary skill in the art.

FIG. 1 illustrates a side view of an ultrasound imaging system, according to some embodiments. In some embodiments, the ultrasound imaging system 100 includes an ultrasound probe 140 coupled to a console 110. In some embodiments, the console 110 is coupled to a display 170. The console 110 may be configured to depict ultrasound images on the display 170. In some embodiments, the display 170 may be wired to the console 110 or may be in wireless communication with the console 110. Exemplary wireless communication modalities can include WiFi, Bluetooth, Near Field Communications (NFC), cellular Global System for Mobile Communication ("GSM"), electromagnetic (EM), radio frequency (RF), combinations thereof, or the like.

In some embodiments, the ultrasound probe 140 may be wired to the console 110, in wireless communication with the console 110, or a combination thereof. Exemplary wireless communication modalities are described above. In some embodiments, the ultrasound probe 140 includes a piezoelectric array 164 to produce and receive echoes that can be converted into an ultrasound image. However, other modalities that produce and receive echoes that can be converted into an ultrasound image or that acquire an ultrasound image are considered. The ultrasound probe 140 may be configured to transmit a plurality of ultrasound images to the console 110. In some embodiments, the ultrasound probe 140 may be wired to the console 110 by an ultrasound probe connector 142.

In some embodiments, the ultrasound probe 140 is coupled to the console by the ultrasound probe connector 142. In some embodiments, the proximal end of the ultrasound probe connector 142 is coupled to the console 110 and the distal end of the ultrasound probe connector 142 is coupled to the ultrasound probe 140. In some embodiments, the ultrasound probe connector 142 includes optical fibers 147 extending from the console 110 to the ultrasound probe 140. More particularly, in some embodiments, the ultrasound probe connector 142 includes one or more optical fiber cores 136, where each are configured with an array of sensors (reflective gratings), which are spatially distributed over a prescribed length of the core fiber to generally sense external strain on those regions of the core fiber occupied by the sensor. Each optical fiber core is configured to receive light (e.g., broadband light, infrared light, near infrared light, etc.) from the console 110 during advancement of the ultrasound probe 140 over the target area 130, where the light propagates along at least a partial distance of the optical fiber core toward the distal end. For purposes of clarity, the terms incident light or broadband incident light may be utilized in the description below; however, infrared light and near infrared light may be alternatively utilized. Given that each sensor positioned along the optical fiber core is configured to reflect light of a different, specific spectral width, the array of sensors enables distributed measurements throughout the prescribed length of the ultrasound probe connector 142. These distributed measurements may include wavelength shifts having a correlation with strain experienced by the sensor. The reflected light from the sensors (reflective gratings) within an optical fiber core 136 is returned from the ultrasound probe connector 142 for processing by the console 110. The physical state of the ultrasound probe connector 142 may be ascertained based on analytics of the wavelength shifts of the reflected light. For example, the strain caused through bending of the medical instrument and hence angular modification of the optical fiber core, causes different degrees of deformation. The different degrees of deformation alter the shape of the sensors (reflective grating) positioned on the optical fiber core, which may cause variations (shifts) in the wavelength of the reflected light from the sensors positioned on the optical fiber core. The optical fiber core may comprise a single optical fiber, or a plurality of optical fibers (in which case, the optical fiber core is referred to as a "multi-core optical fiber").

In some embodiments, the ultrasound probe connector 142 includes an interconnect 145, including a connector 146 that, when coupled to the interconnect 145, establishes optical connectivity between one or more optical fibers 147 (hereinafter, "optical fiber(s)") included as part of the interconnect 145 and core fibers 137 deployed within optical fiber core 136 of ultrasound probe connector 142. Alternatively, a different combination of connectors, including one or more adapters, may be used to optically connect the optical fiber(s) 147 to the core fibers 137 of the ultrasound probe connector 142. As discussed herein, the optical fiber core 136 may be comprised of core fibers $137_1$-$137_M$ (M=1 for a single core, and M≥2 for a multi-core), where the core fibers $137_1$-$137_M$ may collectively be referred to as core fiber(s) 137. In some embodiments, the ultrasound probe connector 142 includes broadband incident light 155 and reflected light signals 150. In some embodiments, the console 110 includes optical logic 180 which may be configured to transmit broadband incident light 155 along the optical fibers 147 and receive reflected light signals 150 that will be described in more detail herein. In some embodiments, the one or more core fibers 137 may be configured to provide a representation of the physical location or physical state of the ultrasound probe 140 in relation to a point of reference within the target area 130. In some embodiments, the reflected light signals 150 pertain to various discrete portions (e.g., specific, "spectral widths" or "wavelengths") of broadband incident light 155. The console 110 may be configured to associate the representation of the physical location or physical state of the ultrasound probe 140 from characteristics of the reflected light signals 150 with the ultrasound images taken by the ultrasound probe to constitute a two-dimensional (2-D) or three-dimensional (3D) representation of a target area 130, the physical location or the physical state of the ultrasound probe 140, as will be further described in more detail herein.

In some embodiments, the core fiber utilizes a plurality of sensors and each sensor is configured to reflect a different spectral range of the incident light (e.g., different light frequency range). Based on the type and degree of strain asserted on each core fiber, the sensors associated with that core fiber may alter (shift) the wavelength of the reflected light to convey the type and degree of stain on that core fiber at those locations of the ultrasound probe connector 142 occupied by the sensors. The sensors are spatially distributed at various locations of the core fiber between a proximal end of the ultrasound probe connector 142 and a distal end of the ultrasound probe connector 142 so that shape sensing of the ultrasound probe connector 142 may be conducted based on analytics of the wavelength shifts. In some embodiments, the shape sensing functionality is paired with the ability to simultaneously pass an ultrasound signal through the same member (ultrasound probe connector 142) through conductive medium included as part of the ultrasound probe connector 142. In some embodiments, the optical fibers 147 include one or more core fibers. In some embodiments, each of the one or more core fibers 137 includes a plurality of sensors distributed along a longitudinal length of a corresponding core fiber and each sensor of the plurality of sensors is configured to reflect a light signal of a different spectral width based on received incident light, and change a characteristic of the reflected light signal for use in determining a physical state of the optical fiber. In some embodiments, the optical fiber is a single-core optical fiber, and wherein the incident light is provided in pulses. In some embodiments, the console 110 may be configured to continuously associate a shape of the optical fibers with an obtained ultrasound image. The associated pairings of {optical fiber shape, ultrasound image} may be provided to the console 110 such that a shape sensing logic 254 may generate a 3D visualization by stitching the ultrasound images together based on the optical fiber shape associated with each ultrasound image, starting from a point of reference.

In some embodiments, the ultrasound imaging system 100 includes one or more electromagnetic sensors 160 configured to detect a magnetic field over the target area 130, generated by a reference magnet 166. In some embodiments, the reference magnet 166 may include a plurality of magnets. In some embodiments, the reference magnet 166 may include a passive magnet, an electromagnet, magnetized metal, non-magnetized metal or the like. In some embodiments, the console 110 may be configured to use the detected magnetic field strength values to generate a 3D ultrasound image of the target area 130. In some embodiments, the console 110 may be configured to associate a measured magnetic field strength value with an ultrasound image, to generate a 3D ultrasound image. In some embodiments, the reference magnet 166 may be included in a cuff 168, configured to wrap around a portion of the target area 130. In some embodiments, the one or more electromagnetic sensors 160 are coupled to the ultrasound probe 140. The one or more electromagnetic sensors 160 are configured to detect and transmit to the console 110, magnetic field strength values of the reference magnet 166, in relation to the ultrasound probe 140.

In some embodiments, the ultrasound probe 140 may include one or more accelerometers 162. The one or more accelerometers 162 may be configured to detect acceleration of the ultrasound probe 140, as it moves over the target area 130. The one or more accelerometers 162 may be configured to transmit the acceleration data to the console 110. In some embodiments, the console 110 may be configured to use the acceleration data of the ultrasound probe 140 to determine proximity of the ultrasound probe 140 to a reference point in constructing the 3D ultrasound image of the target area that will be described in more detail herein.

In some embodiments, the ultrasound imaging system 100 may be configured to use one or more of: the one or more optical fibers 147, the one or more electromagnetic sensors 160 or the one or more accelerometers 162 to create a 3D ultrasound image of the target area 130. The user may place an elongate medical device 114 within the target area 130, using the ultrasound imaging system 100 to guide the elongate medical device 114 to the proper anatomical location. In some embodiments, an elongate medical device 114 may be configured to be placed in the target area 130 as a point of reference and the ultrasound imaging system 100 may be configured to generate the 3D ultrasound image. In some embodiments, the ultrasound imaging system 100 may be configured to generate the 3D ultrasound image, and the elongate medical device 114 may be configured to be placed in the target area 130. In some embodiments, the elongate medical device 114 includes the ultrasound probe 140, a catheter, a stylet, a needle, a guidewire, or a combination thereof. In some embodiments, the console 110 may be configured to track, using one or more of the ultrasound probe 140, the one or more optical fibers 147, the one or more electromagnetic sensors 160, the one or more accelerometers, or the elongate medical device 114 as the elongate medical device 114 is placed in the target area 130.

Figure 2:
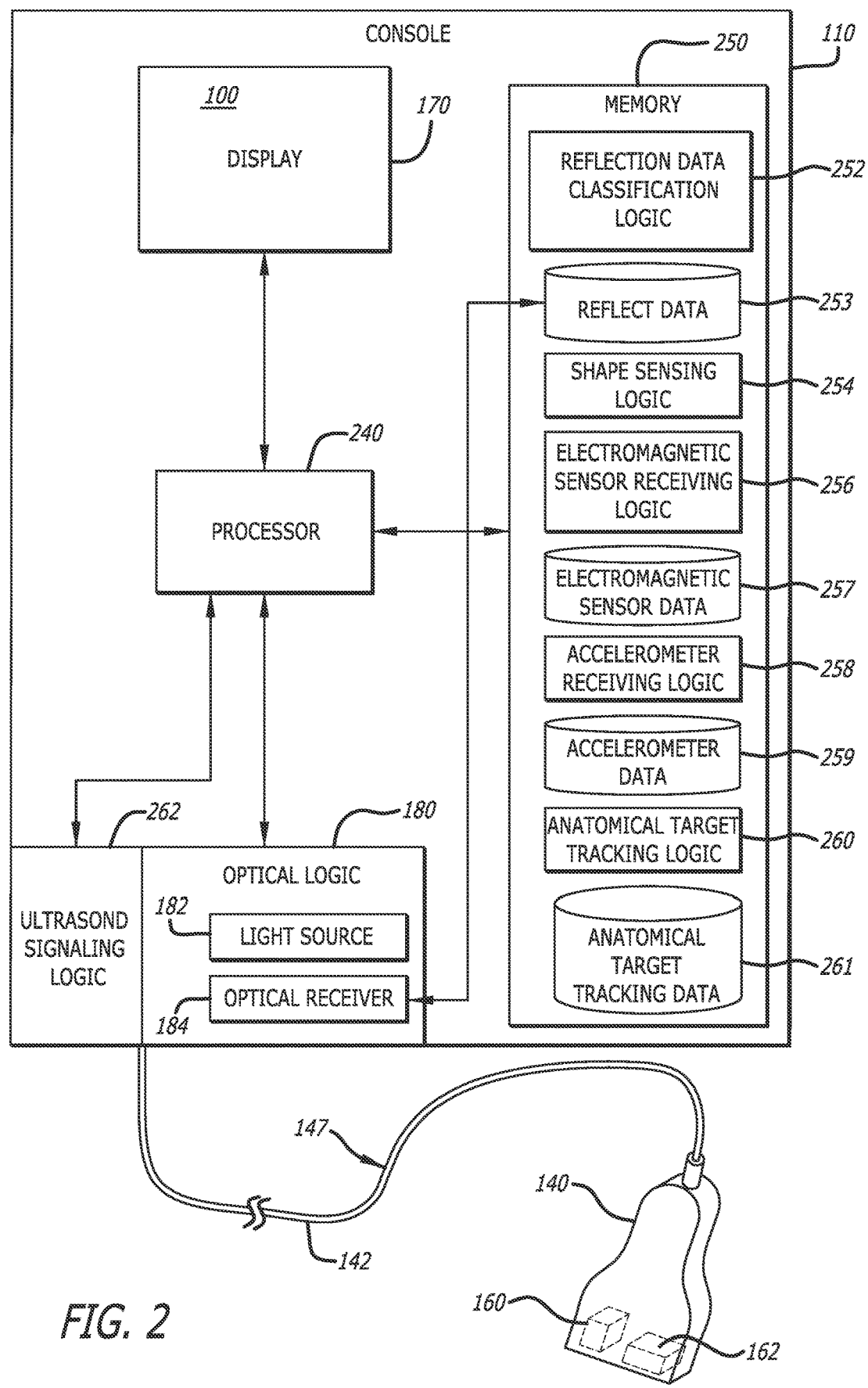
FIG. 2 illustrates a block diagram of components of the ultrasound imaging system, in accordance with some embodiments.

FIG. 2. illustrates a block diagram of components of the ultrasound imaging system 100, in accordance with some embodiments. In some embodiments, the ultrasound imaging system 100 includes the console 110, the ultrasound probe 140 including one or more of one or more accelerometers 162 or one or more electromagnetic sensors 160, and the optical fiber 147 within the ultrasound probe connector 142. The console 110 is shown to include one or more processors 240, the display 170, an ultrasound signaling logic 262 configured to receive transmitted ultrasound signals, an optical logic 180 and non-transitory, computer-readable medium ("memory") 250. The memory 250 is configured to store one or more logic modules including a reflection data classification logic 252, shape sensing logic 254, electromagnetic sensor receiving logic 256, accelerometer receiving logic 258, and anatomical target tracking logic 260. Further, the memory 250 may include data stores such as reflect data 253, electromagnetic sensor data 257, accelerometer data 259 or anatomical target tracking data 261.

In some embodiments, the optical logic 180 is configured to support operability of the ultrasound probe 140 and enable the return of information to the console 110, which may be used to determine the physical location or physical state associated with the ultrasound probe 140. In some embodiments, as the ultrasound probe 140 is coupled to the console 110 by the ultrasound probe connector 142, determining the physical location or physical state of the distal end of the ultrasound probe connector 142 will determine the physical location or physical state of the ultrasound probe 140. The physical state of the ultrasound probe 140 may be based on changes in characteristics of the reflected light signals 150 received from the ultrasound probe connector 142. The characteristics may include shifts in wavelength caused by strain on certain regions of the core fibers 137 of the optical fiber core 136 integrated within the ultrasound probe connector 142, which may be used to determine (through computation or extrapolation of the wavelength shifts) the physical state or location of the ultrasound probe 140. As a result, the physical state or physical location of the ultrasound probe 140 may be determined as the physical location or physical state of the ultrasound probe 140 will mirror that of the ultrasound probe 140, which is advancing over the target area 130.

More specifically, as illustrated in FIG. 2, the optical logic 180 includes a light source 182. The light source 182 is configured to transmit the broadband incident light 155 for propagation over the optical fiber(s) 147 included in the interconnect 145, which is optically connected to multiple core fibers 137 of the optical fiber core 136 within the ultrasound probe connector 142. In one embodiment, the light source 182 is a tunable swept laser, although other suitable light source can also be employed in addition to a laser, including semi-coherent light sources, LED light sources, etc.

In some embodiments, the optical logic 180 further includes an optical receiver 184 (e.g., a photodetector such as a positive-intrinsic-negative "PIN" photodiode, avalanche photodiode, etc.) Herein, the optical receiver 184 is configured to receive returned optical signals, namely reflected light signals received from optical fiber-based reflective gratings (sensors) fabricated within each of the core fibers 137 of the optical fiber core 136 and translate the reflected light signals 150 into reflect data 253, namely data in the form of electrical signals representative of the reflected light signals including wavelength shifts caused by strain. The reflected light signals 150 associated with different spectral widths include reflected light signals provided from sensors positioned in the center core fiber (reference) of the ultrasound probe connector 142 and reflected light signals provided from sensors positioned in the outer core fibers of the ultrasound probe connector 142, as described below.

As shown in FIG. 2, both the light source 182 and the optical receiver 184 are operably connected to the processor 240, which governs their operation. Also, the optical receiver 184 is operably coupled to provide the reflect data 253 to the memory 250 for storage and processing by the reflection data classification logic 252. The reflection data classification logic 252 may be configured to identify which core fibers pertain to which of the received reflect data 253 and segregate the reflect data 253 provided from reflected light signals 150 pertaining to similar regions of the ultrasound probe connector 142 and/spectral widths into analysis groups.

In some embodiments, the shape sensing logic 254 is configured to compare wavelength shifts measured by sensors deployed in each outer core fiber at the same measurement region of the connection between the console 110 and the ultrasound probe 140 to the wavelength shift at the center core fiber positioned along central axis and operating as a neutral axis of bending. From these analytics, the shape sensing logic 254 may determine the shape the core fibers have taken in relation to a point of reference and may further determine the current physical location of the ultrasound probe 140 in 3D space for rendering on the display 170. In some embodiments, the point of reference may be user provided, user generated, determined by the console 110 (e.g., the reference magnet 166, the ultrasound probe 140, one or more anatomical targets 400, the elongate medical device 114, or the like). It is contemplated that other processes and procedures may be performed to utilize the wavelength shifts as measured by the sensors along each of the core fibers 137 to render appropriate changes in the physical state of the ultrasound probe connector 142 between the console 110 and the ultrasound probe 140.

In some embodiments, the electromagnetic sensor receiving logic 256 receives measured magnetic field strength values of the reference magnet 166 measured by the one or more electromagnetic sensors 160. The electromagnetic sensor receiving logic 256 correlates each measured magnetic field strength value with a transmitted ultrasound image taken by the ultrasound probe 140 at the specific measured magnetic field strength value location. In some embodiments, the electromagnetic sensor data 257 stores each correlated magnetic field strength value with the correlated ultrasound image. In some embodiments, the console 110 can access the electromagnetic sensor data 257 to compile the 3D ultrasound image. In some embodiments, the electromagnetic sensor receiving logic 256 may be configured to use the ultrasound images correlated with the measured magnetic field strength values to compile the 3D ultrasound image.

In some embodiments, the accelerometer receiving logic 258 receives measured acceleration values from the one or more accelerometers 162 coupled to the ultrasound probe 140. The accelerometer receiving logic 258 may be configured to correlate each measured acceleration value with a transmitted ultrasound image taken by the ultrasound probe 140 at the specific measured acceleration value location. In some embodiments, the accelerometer receiving logic 258 may be configured to determine based on the measured acceleration values if the ultrasound probe 140 has moved in 3D space relative to the last ultrasound image taken. In some embodiments, the accelerometer receiving logic 258 may be configured to use the ultrasound images associated with the measured acceleration values to generate the 3D ultrasound image. In some embodiments, the accelerometer data 259 stores each correlated acceleration value with the correlated ultrasound image. In some embodiments, the console 110 can access the accelerometer data 259 to compile the 3D ultrasound image.

In some embodiments, the anatomical target tracking logic 260 identifies and distinguishes anatomical targets such as veins, arteries, bones, tendons, ligaments, nerves, or the like on the transmitted ultrasound images. In some embodiments, the anatomical target tracking logic 260 may be configured to automatically identify and distinguish anatomical targets. In some embodiments, the anatomical target tracking logic 260 may be configured by user selection to identify and distinguish anatomical targets. The anatomical target tracking logic 260 may be configured to select a vein, artery, another anatomical target or the like as a point of reference, relative to the ultrasound probe 140. The anatomical target tracking logic 260 may be configured to provide feedback to a user if the ultrasound probe 140 has moved relative to the selected point of reference. The anatomical target tracking logic 260 may be configured to detect ultrasound probe movement including probe tilt, probe drift, and probe twist. In some embodiments, the anatomical target tracking logic 260 may be configured detect tissue compression, tissue decompression, or the location of the identified anatomical targets. In some embodiments, the anatomical target tracking data 261 stores each correlated distance value from the one or more anatomical targets with the correlated ultrasound image. In some embodiments, the console 110 can access the anatomical target tracking data 261 to compile the 3D ultrasound image.

Figure 3:
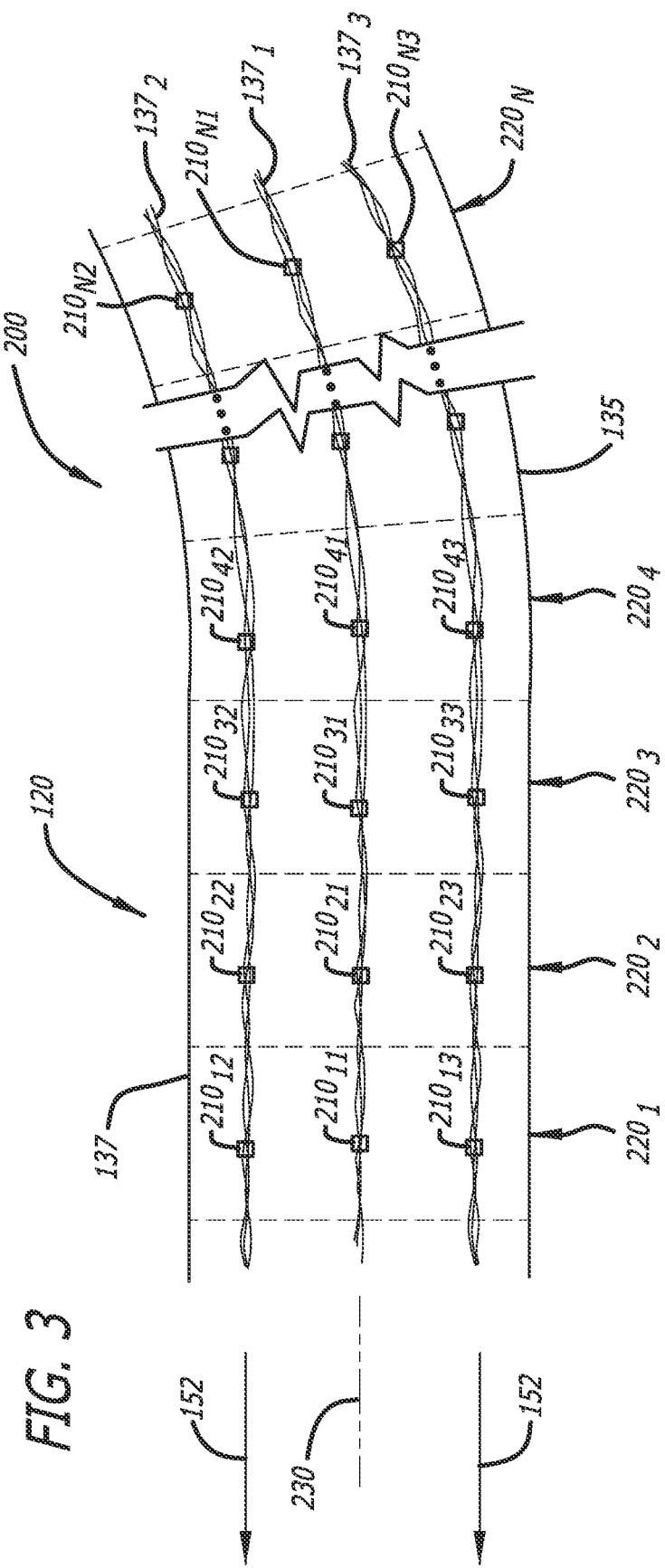
FIG. 3 illustrates an exemplary embodiment of a structure of a section of the multi-core optical fiber included within the ultrasound probe connector, in accordance with some embodiments.

FIG. 3 illustrates an exemplary embodiment of a structure of a section of the multi-core optical fiber included within the ultrasound probe connector 142, in accordance with some embodiments. The multi-core optical fiber section 200 of the optical fiber core 136 depicts certain core fibers $137_1$-$137_M$ (M≥2, M=4 as shown) along with the spatial relationship between sensors (e.g., reflective gratings) $210_{11}$-$210_{NM}$ (N≥2; M≥2) present within the core fibers $137_1$-$137_M$, respectively. In more detail, each sensor may operate as a reflective grating such as a fiber Bragg grating (FBG), namely an intrinsic sensor corresponding to a permanent, periodic refractive index change inscribed into the core fiber. Stated differently, the sensor operates as a light reflective mirror for a specific spectral width (e.g., a specific wavelength or specific range of wavelengths). As a result, as broadband incident light 155 is supplied by an optical light source 182 and propagates through a particular core fiber, upon reaching a first sensor of the distributed array of sensors for that core fiber, light of a prescribed spectral width associated with the first sensor is reflected back to an optical receiver within the console, including the display and the optical light source. The remaining spectrum of the incident light continues propagation through the core fiber toward a distal end of the ultrasound probe connector 142. The remaining spectrum of the incident light may encounter other sensors from the distributed array of sensors, where each of these sensors is fabricated to reflect light with different specific spectral widths to provide distributed measurements, as described above.

As shown in FIG. 3, the section 200 is subdivided into a plurality of cross-sectional regions $220_1$-$220_N$, where each cross-sectional region $220_1$-$220_N$ corresponds to reflective gratings $210_{11}$-$210_{14}$ ... $210_{N1}$-$210_{N4}$. Some or all of the cross-sectional regions $220_1$ ... $220_N$ may be static (e.g., prescribed length) or may be dynamic (e.g., vary in size among the regions $220_1$ ... $220_N$). A first core fiber $137_1$ is positioned substantially along a center (neutral) axis 230 while core fiber $137_2$ may be oriented within the cladding of the multi-core optical fiber 137, from a cross-sectional, front-facing perspective, to be position on "top" the first core fiber $137_1$. In this deployment, the core fibers $137_3$ and $137_4$ may be positioned "bottom left" and "bottom right" of the first core fiber $137_1$.

Referencing the first core fiber $137_1$ as an illustrative example, when the ultrasound probe connector 142 is operative, each of the reflective gratings $210_1$-$210_N$ reflects light for a different spectral width. As shown, each of the gratings $210_{1i}$-$210_{Ni}$ (1≤i≤M) is associated with a different, specific spectral width, which would be represented by different center frequencies of $f_1$ ... $f_N$, where neighboring spectral widths reflected by neighboring gratings are non-overlapping according to one embodiment of the disclosure.

Herein, positioned in different core fibers $137_2$-$137_3$ but along at the same cross-sectional regions $220$-$220_N$ of the multi-core optical fiber 137, the gratings $210_{12}$-$210_{N2}$ and $210_{13}$-$210_{N3}$ are configured to reflect incoming light at same (or substantially similar) center frequency. As a result, the reflected light returns information that allows for a determination of the physical state of the optical fiber 137 (and the ultrasound probe connector 142) based on wavelength shifts measured from the returned, reflected light. In particular, strain (e.g., compression or tension) applied to the multi-core optical fiber 137 (e.g., at least core fibers $137_2$-$137_3$) results in wavelength shifts associated with the returned, reflected light. Based on different locations, the core fibers $137_1$-$137_4$ experience different types and degree of strain based on angular path changes as the ultrasound probe 140 moves over the target area 130.

For example, with respect to the multi-core optical fiber section 200 of FIG. 3, in response to movement of the ultrasound probe 140 and thus ultrasound probe connector 142 in the lateral direction, the second core fiber $137_2$ of the multi-core optical fiber 137 with the shortest radius during movement (e.g., core fiber closest to a direction of angular change) would exhibit compression (e.g., forces to shorten length). At the same time, the third core fiber $137_3$ with the longest radius during movement (e.g., core fiber furthest from the direction of angular change) would exhibit tension (e.g., forces to increase length). As these forces are different and unequal, the reflected light from reflective gratings $210_{N2}$ and $210_{N3}$ associated with the core fiber $137_2$ and $137_3$ will exhibit different changes in wavelength. The differences in wavelength shift of the reflected light signals 150 can be used to extrapolate the physical configuration of the ultrasound probe connector 142 by determining the degrees of wavelength change caused by compression/tension for each of the periphery fibers (e.g., the second core fiber $137_2$ and the third core fiber $137_3$) in comparison to the wavelength of the reference core fiber (e.g., first core fiber $137_1$) located along the neutral axis 230 of the multi-core optical fiber 137. These degrees of wavelength change may be used to extrapolate the physical state of the ultrasound probe connector 142. The reflected light signals 150 are reflected back to the console 110 via individual paths over a particular core fiber $137_1$-$137_M$.

Figure 4B:
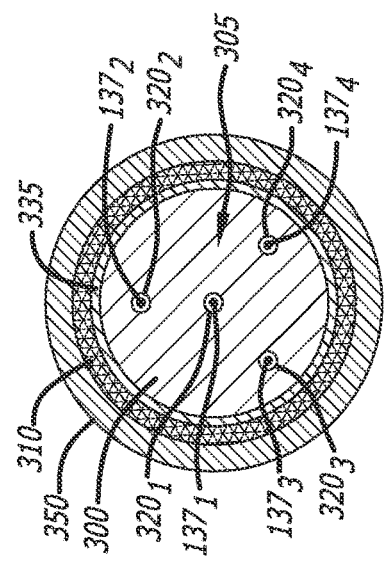
FIG. 4B illustrates a cross sectional view of the ultrasound probe connector of FIG. 3, in accordance with some embodiments.
Figure 4A:
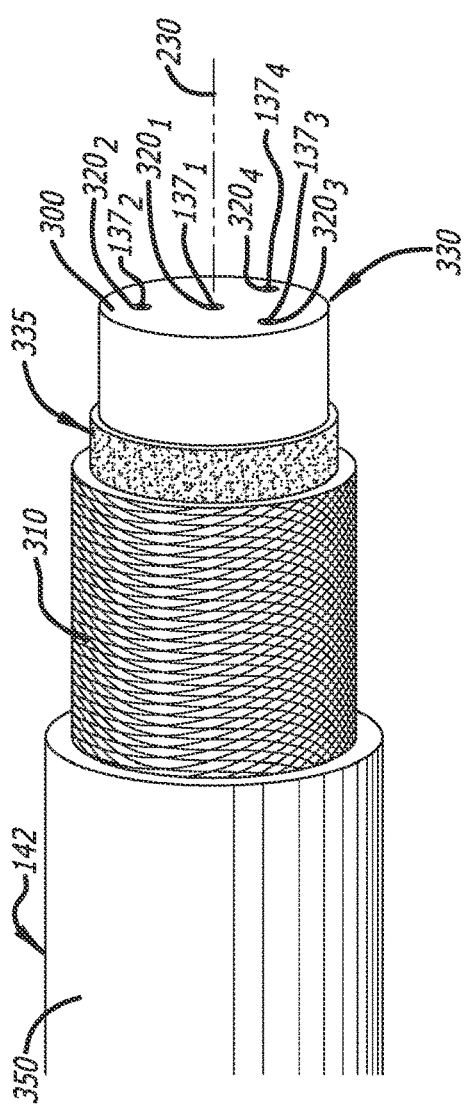
FIG. 4A illustrates an exemplary embodiment of the ultrasound probe connector supporting both an optical and ultrasound signaling, in accordance with some embodiments.

FIG. 4A is an exemplary embodiment of the ultrasound probe connector 142 supporting optical signaling and ultrasound signaling, in accordance with some embodiments. Herein, the ultrasound probe connector 142 features a centrally located multi-core optical fiber 137, which includes a cladding 300 and a plurality of core fibers $137_1$-$137_M$ (M≥2; M=4) residing within a corresponding plurality of lumens $320_1$-$320_M$. While the multi-core optical fiber 137 is illustrated within four (4) core fibers $137_1$-$137_4$, a greater number of core fibers $137_1$-$137_M$ (M>4) may be deployed to provide a more detailed three-dimensional sensing of the physical state (e.g., shape, etc.) of the multi-core optical fiber 137 and the ultrasound probe connector 142 deploying the optical fiber 137, a greater number of core fibers $137_1$-$137_M$ (M>4) may be deployed. In some embodiments, the multi-core optical fiber 137 may be configured to be encapsulated within a concentric braided tubing 310 positioned over a low coefficient of friction layer 335. The braided tubing 310 may feature a "mesh" construction, in which the spacing between the intersecting conductive elements is selected based on the degree of rigidity desired for the ultrasound probe connector 142, as a greater spacing may provide a lesser rigidity, and thereby, a more pliable ultrasound probe connector 142.

In some embodiments, as shown in FIGS. 4A-4B, the core fibers $137_1$-$137_4$ include a central core fiber $137_1$ and a plurality of periphery core fibers $137_2$-$137_4$, which are maintained within lumens $320_1$-$320_4$ formed in the cladding 300. In some embodiments, one or more of the lumen $320_1$-$320_4$ may be configured with a diameter sized to be greater than the diameter of the core fibers $137_1$-$137_4$. By avoiding a majority of the surface area of the core fibers $137_1$-$137_4$ from being in direct physical contact with a wall surface of the lumens $320_1$-$320_4$, the wavelength changes to the incident light are caused by angular deviations in the multi-core optical fiber 137 thereby reducing influence of compression and tension forces being applied to the walls of the lumens $320_1$-$320_M$, not the core fibers $137_1$-$137_M$ themselves.

As further shown in FIGS. 4A-4B, the core fibers $137_1$-$137_4$ may include central core fiber $137_1$ residing within a first lumen $320_1$ formed along the first neutral axis 230 and a plurality of core fibers $137_2$-$137_4$ residing within lumens $320_2$-$320_4$ each formed within different areas of the cladding 300 radiating from the first neutral axis 230. In general, the core fibers $137_2$-$137_4$, exclusive of the central core fiber $137_1$, may be positioned at different areas within a cross-sectional area 305 of the cladding 300 to provide sufficient separation to enable three-dimensional sensing of the multi-core optical fiber 137 based on changes in wavelength of incident light propagating through the core fibers $137_2$-$137_4$ and reflected back to the console for analysis.

For example, where the cladding 300 features a circular cross-sectional area 305 as shown in FIG. 4B, the core fibers $137_2$-$137_4$ may be positioned substantially equidistant from each other as measured along a perimeter of the cladding 300, such as at "top" (12 o'clock), "bottom-left" (8 o'clock) and "bottom-right" (4 o'clock) locations as shown. Hence, in general terms, the core fibers $137_2$-$137_4$ may be positioned within different segments of the cross-sectional area 305. Where the cross-sectional area 305 of the cladding 300 has a distal tip 330 and features a polygon cross-sectional shape (e.g., triangular, square, rectangular, pentagon, hexagon, octagon, etc.), the central core fiber $137_1$ may be located at or near a center of the polygon shape, while the remaining core fibers $137_2$-$137_M$ may be located proximate to angles between intersecting sides of the polygon shape. Referring still to FIGS. 4A-4B, operating as the conductive medium for the ultrasound probe connector 142, the braided tubing 310 provides mechanical integrity to the multi-core optical fiber 137 and may be configured to operate as a conductive pathway for ultrasound signals. The cladding 300 and the braided tubing 310, which is positioned concentrically surrounding a circumference of the cladding 300, are contained within the same insulating layer 350. The insulating layer 350 may be a sheath or conduit made of protective, insulating (e.g., non-conductive) material that encapsulates both for the cladding 300 and the braided tubing 310, as shown.

Figure 5:
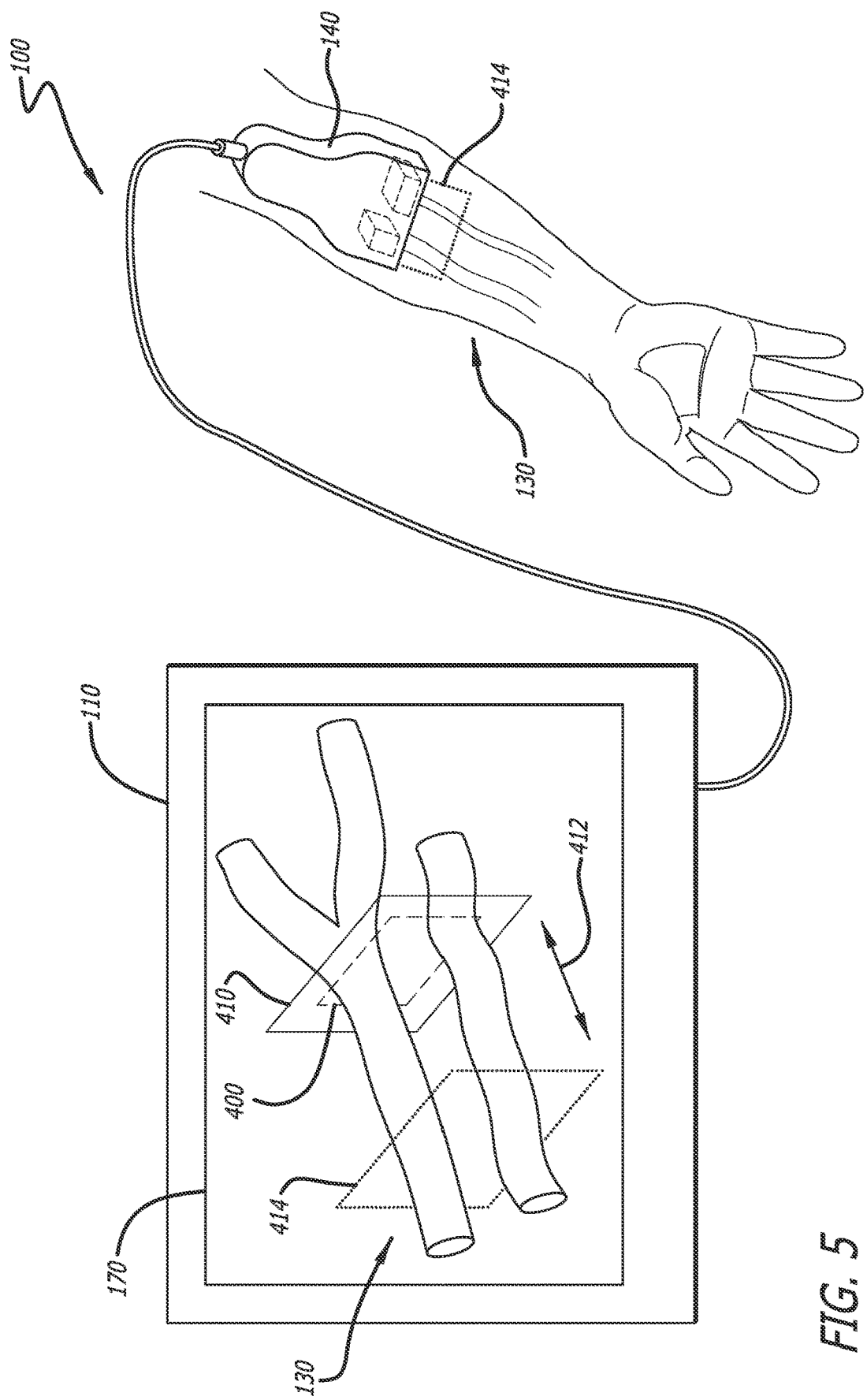
FIG. 5 illustrates a side view of various components of the ultrasound imaging system, in accordance with some embodiments.

FIG. 5 illustrates a side view of various components of the ultrasound imaging system 100 including the ultrasound probe 140, in accordance with some embodiments. In some embodiments, the ultrasound imaging system 100 can include anatomical target tracking capabilities. In some embodiments, the console 110 can be configured to automatically identify and distinguishes veins, arteries, other anatomical targets or the like on the ultrasound images. The console 110 can be configured to automatically identify one or more anatomical targets 400 on a static or dynamic ultrasound image. In identifying one or more anatomical targets 400, the console 110 may be configured to select the one or more anatomical targets 400 as a point of reference 410 relative to the ultrasound probe 140. As the ultrasound probe 140 is moved along the target area 130, the console 110 may be configured to track the ultrasound probe 140 relative to the point of reference 410. In some embodiments, the console 110 may be configured to provide feedback to the user if the ultrasound probe 140 drifts relatives to the point of reference 410. In some embodiments, the console 110 may be configured to depict the one or more anatomical targets 400 of the target area 130 on the display 170. In some embodiments, the user may select the one or more anatomical targets 400 by manual user input including selecting on the display 170, button press, voice activation, or the like. In some embodiments, the ultrasound probe 140 or the console 110 may be configured to continuously associate a distance from the point of reference 410, being the one or more anatomical targets 400, with an obtained ultrasound image 414. The associated pairings of {distance from point of reference, ultrasound image} may be provided to the console 110 such that the anatomical target tracking logic 260 may generate a 3D visualization by stitching the ultrasound images together based on the distance 412 from the point of reference associated with each image, starting from a point of reference. The console 110 may be configured to detect ultrasound probe movement including probe tilt, probe drift, or probe twist, relative to the one or more anatomical targets 400. In some embodiments, the console 110 may be configured to detect tissue compression, tissue decompression, communication information on the one or more anatomical target locations, or a combination thereof. In some embodiments, the console 110 may be configured to use the point of reference 410 to build a 3D image of the target area 130 for display on the display 170. In some embodiments, the one or more anatomical targets 400 may be configured to be a landmark for a user to direct the ultrasound probe 140 to when placing the elongate medical device 114.

Figure 6:
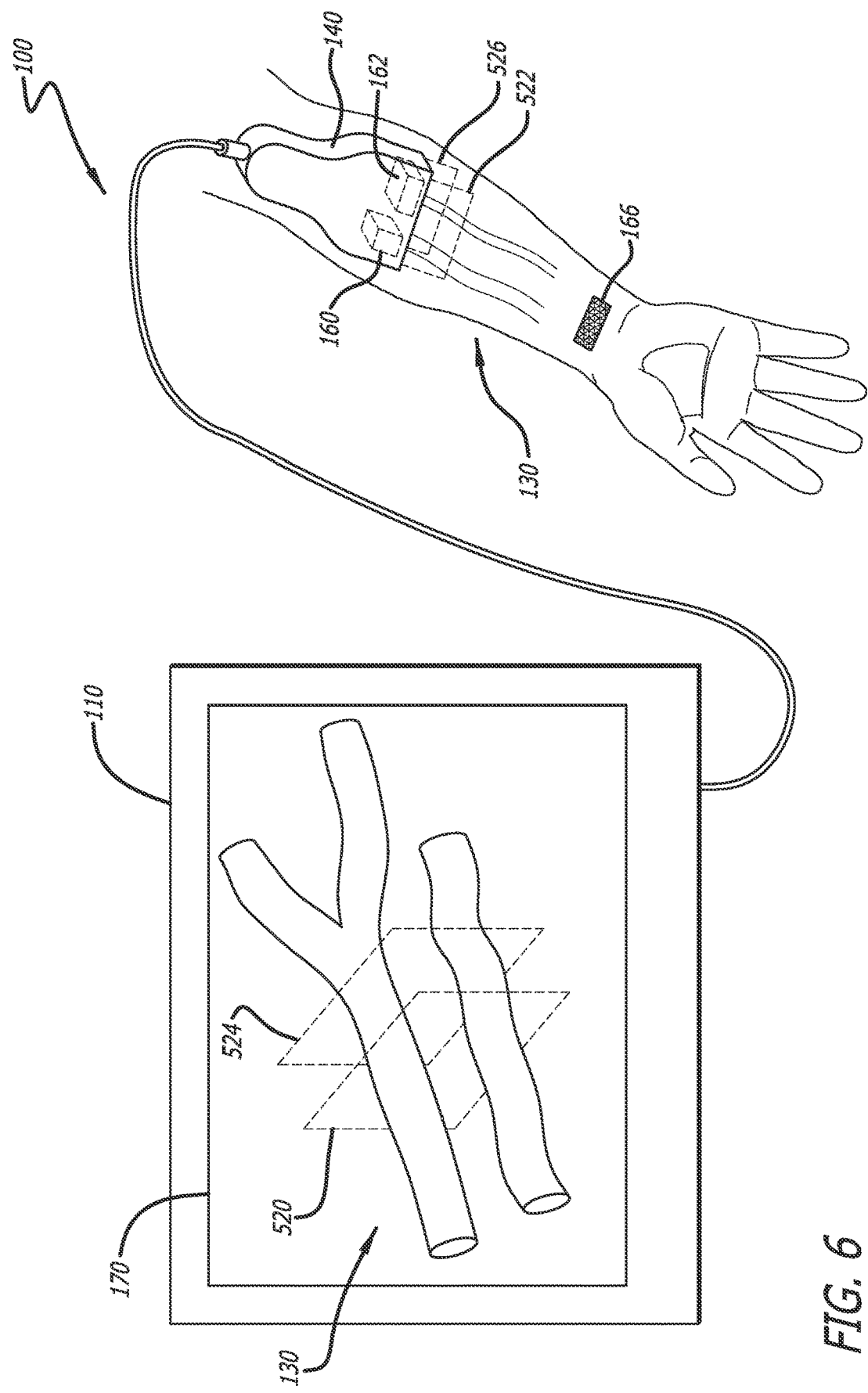
FIG. 6 illustrates a side view of various components of the ultrasound imaging system including the ultrasound probe having one or more electromagnetic sensors and one or more accelerometers, in accordance with some embodiments.

FIG. 6 illustrates a side view of various components of the ultrasound imaging system including the ultrasound probe 140 having one or more electromagnetic sensors 160 and one or more accelerometers 162, in accordance with some embodiments. In some embodiments, the ultrasound probe 140 includes the one or more electromagnetic sensors 160 configured to detect a magnetic field, the one or more accelerometers 162 configured to detect ultrasound probe acceleration or a combination thereof. As illustrated in FIG. 6, the ultrasound imaging system 100 includes a reference magnet 166, configured to generate the magnetic field over the target area 130 detectable by the one or more electromagnetic sensors 160, as the ultrasound probe 140 images the target area 130. As the reference magnet 166 remains stationary relative to the target area 130 during use of the ultrasound probe 140, the reference magnet 166 acts as a point of reference for the ultrasound probe 140 and the console 110. In some embodiments, the reference magnet 166 may be configured to include an electromagnet that is coupled to a power supply, increasing the strength of the magnetic field. Increasing the strength of the magnetic field would allow the ultrasound probe 140 to be used at greater distances from the reference magnet 166.

When the ultrasound probe 140 is moved along the target area 130, the strength of the magnetic field as detected by the one or more electromagnetic sensors 160 changes. The ultrasound probe 140 may be specifically configured to associate a detected magnetic field strength with a particular ultrasound image (received as an echo). Further, the ultrasound probe 140 may be configured to continuously associate a strength of a detected magnetic field with an obtained ultrasound image. The associated pairings of {detected magnetic field strength, ultrasound image} may be provided to the console 110 such that the electromagnetic sensor receiving logic 256 may generate a 3D visualization by stitching the ultrasound images together based on the magnetic field strength associated with each ultrasound image, starting from the point of reference. In other words, the electromagnetic sensor receiving logic 256 may properly align the ultrasound images based on the detected magnetic field strength associated with each. For example, at a first magnetic field strength value 522, the ultrasound probe 140 may transmit a first image 520 to the console 110. At a second magnetic field strength value 526, the ultrasound probe 140 may transmit a second image 524 to the console 110. The console 110 may be configured to properly align the first image 520 and the second image 524 to create a 3D ultrasound image. In particular, the detected magnetic field strength value provides an indication of a location of the ultrasound image in the target area 130 in relation to the stationary reference magnet 166, which is used to align the ultrasound images.

In some embodiments, as illustrated in FIG. 6, the ultrasound probe 140 may include one or more accelerometers 162. The one or more accelerometers 162 may be configured detect and transmit to the console 110, acceleration values of the ultrasound probe 140 as the probe 140 is moving over the target area 130. In some embodiments, the ultrasound probe 140 or the console 110 may be configured to continuously associate an acceleration value with an obtained ultrasound image. The associated pairings of {acceleration value, ultrasound image} may be provided to the console 110 such that the accelerometer receiving logic 258 may generate a 3D visualization by stitching the ultrasound images together based on the acceleration value associated with each ultrasound image, starting from the point of reference. In some embodiments, the console 110 may be configured to determine using the accelerometer receiving logic 258, when the ultrasound probe 140 is in motion. In some embodiments, the console 110 may be configured to determine ultrasound probe 140 motion using the detected magnetic field strength values, acceleration values, or a combination thereof. In some embodiments, ultrasound probe motion includes ultrasound probe tilt, ultrasound probe drift, ultrasound probe twist or a combination thereof.

Figure 7:
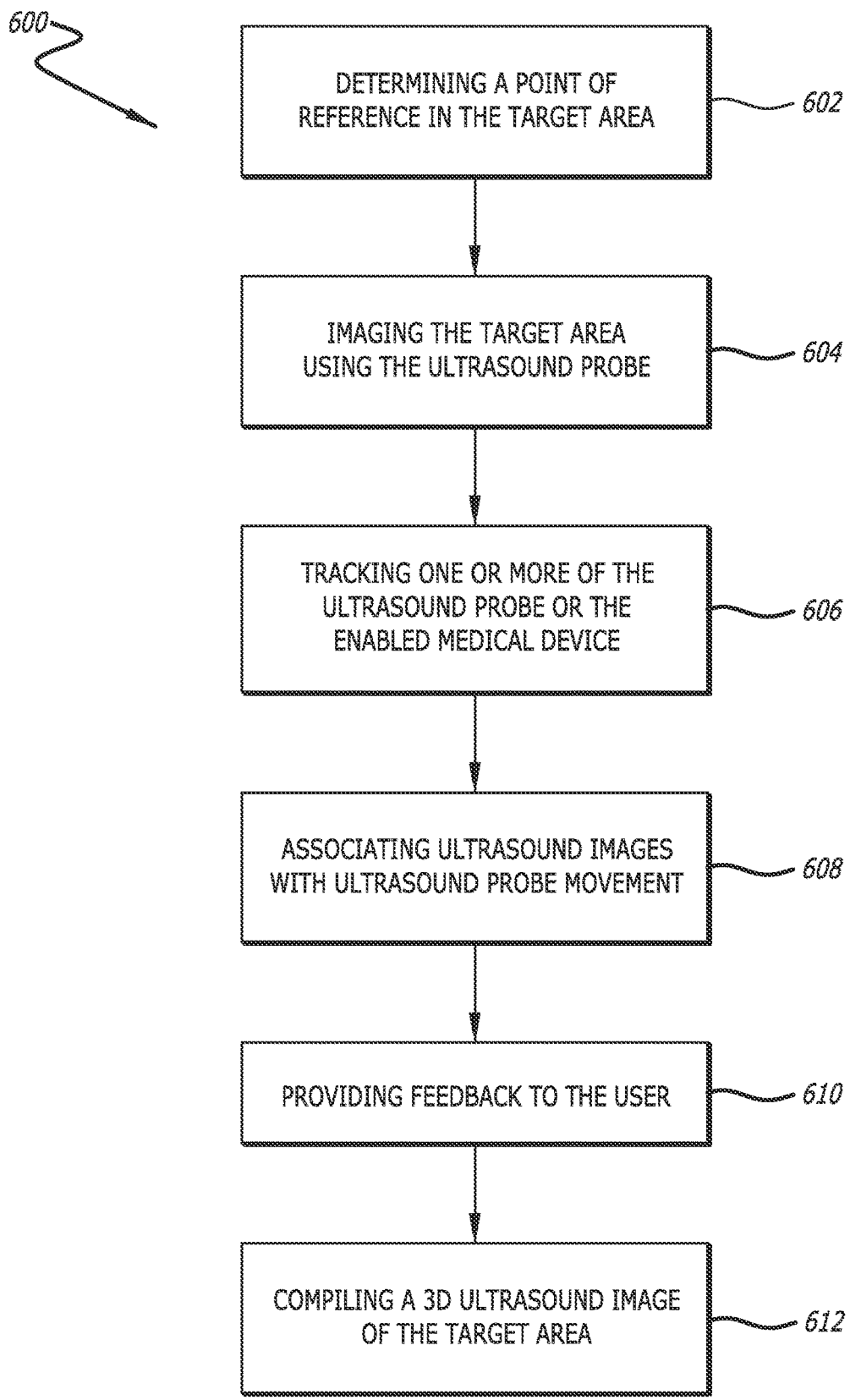
FIG. 7 illustrates a flow chart of an exemplary method of using an ultrasound imaging system to create a 3D ultrasound image, in accordance with some embodiments.

FIG. 7 illustrates a flow chart of an exemplary method of using an ultrasound imaging system to create a 3D ultrasound image of a target area, in accordance with some embodiments. In some embodiments, the method 600 includes determining a point of reference in the target area using one or more of: a reference magnet 166 and one or more electromagnetic sensors 160, one or more accelerometers 162, one or more anatomical targets 400, an ultrasound probe 140, or the elongate medical device 114 (block 602). In some embodiments, the reference magnet 166 is configured to provide a magnetic field over the target area 130 and the one or more electromagnetic sensors 160 may be configured to detect and measure the magnetic field strength. In some embodiments, the elongate medical device 114 includes a catheter, a stylet, a needle or a guidewire.

The method 600 further includes imaging the target area using the ultrasound probe 140 coupled to a console 110 by an ultrasound probe connector 142 having optical fiber 147 including one or more core fibers, the ultrasound probe 140 having one or more electromagnetic sensors 160 or one or more accelerometers 162 (block 604). In some embodiments, imaging the target area 130 can include moving the ultrasound probe 140 over the target area 130.

The method 600 further includes tracking one or more of the ultrasound probe 140 and the elongate medical device 114 (block 606). In some embodiments, tracking one or more of the ultrasound probe 140 and the elongate medical device 114 includes using detected magnetic field strength values, in relation to the reference magnet, to track the ultrasound probe 140 and the elongate medical device 114. In some embodiments, tracking one or more of the ultrasound probe 140 and the elongate medical device 114 includes using the shape of the one or more core fibers taken in relation to the point of reference. In some embodiments, tracking one or more of the ultrasound probe 140 and the elongate medical device 114 includes using the location of the ultrasound probe 140 in relation to the one or more anatomical targets 400 as the point of reference. In some embodiments, tracking one or more of the ultrasound probe 140 and the elongate medical device 114 may include a combination of using the detected magnetic field strength values, the shape of the one or more core fibers in relation to the point of reference or the location of the ultrasound probe in relation to the one or more anatomical targets.

The method 600 includes associating ultrasound images with ultrasound probe movement (block 608). In some embodiments, associating ultrasound images with ultrasound probe movement may include associating ultrasound images with corresponding detected measured magnetic field strength values. In some embodiments, associating ultrasound images with ultrasound probe movement can include associating ultrasound images with the corresponding shape of the one or more core fibers taken in relation to the point of reference. In some embodiments, associating ultrasound images with ultrasound probe movement can include associating ultrasound images with corresponding acceleration values of the ultrasound probe 140. In some embodiments, associating ultrasound images with ultrasound probe movement can include a combination of the foregoing.

The method 600 further includes providing feedback to a user to maintain the ultrasound probe alignment with the target area 130 (block 610). In some embodiments, providing feedback includes audio feedback, visual feedback depicted on the display 170 or a combination thereof. In some embodiments, providing feedback to a user includes using the one or more accelerometers 162 to maintain ultrasound probe alignment within the target area 130. In some embodiments, providing feedback to a user includes using the one or more anatomical targets 400 to maintain ultrasound probe alignment within the target area 130. In some embodiments, providing feedback to a user including indicating ultrasound probe tilt, ultrasound probe drift, ultrasound probe twist or a combination thereof. In some embodiments, providing feedback to a user includes indicating on the display 170, tissue compression, tissue decompression, the location of the identified anatomical target 400 in relation to the ultrasound probe 140, or a combination thereof.

The method 600 further includes compiling a 3D ultrasound image of the target area 130 using the console, the console having one or more processors 240 and non-transitory computer readable medium having stored thereon one or more logic modules (block 612). In some embodiments, the one or more logic modules include one or more of the reflection data classification logic 252, the shape sensing logic 254, the electromagnetic sensor receiving logic 256, the accelerometer receiving logic 258, and the anatomical target tracking logic 260. In some embodiments, the one or more logic modules may be configured to perform one or more of the following: determine the shape of the one or more core fibers taken in relation to the point of reference, transmit and receive optical signals, detect and select one or more anatomical targets as the point of reference, detect measured magnetic field strength values, determine ultrasound probe movement in relation to the point of reference, associate ultrasound probe movement with ultrasound images, and compiling a 3D ultrasound image of the target area. In some embodiments, compiling a 3D ultrasound image of the target area 130 includes using ultrasound images associated with corresponding detected magnetic field strength values, using ultrasound images associated with corresponding shapes of the one or more core fibers in relation to the point of reference, using ultrasound images associated with corresponding detected acceleration values of the ultrasound probe, or a combination thereof. In some embodiments, compiling a 3D ultrasound image of the target area 130 includes compiling a 3D image of the path of the elongate medical device 114. In some embodiments, compiling a 3D ultrasound image of the target area 130 includes displaying additional elongate medical device purchase prediction and elongate medical device purchase confirmation wherein the additional elongate medical device includes a catheter. In some embodiments, compiling a 3D ultrasound image of the target area 130 includes depicting the 3D ultrasound image on the display 170.

While some particular embodiments have been disclosed herein, and while the particular embodiments have been disclosed in some detail, it is not the intention for the particular embodiments to limit the scope of the concepts provided herein. Additional adaptations and/or modifications can appear to those of ordinary skill in the art, and, in broader aspects, these adaptations and/or modifications are encompassed as well. Accordingly, departures may be made from the particular embodiments disclosed herein without departing from the scope of the concepts provided herein.

What is claimed is:

1. An ultrasound imaging system configured to generate a 3D ultrasound image of a target area, comprising:
    an ultrasound probe configured to acquire a plurality of ultrasound images of the target area including one or more anatomical targets, the ultrasound probe coupled to a console by an ultrasound probe connector having an optical fiber including one or more core fibers, the ultrasound probe being a point of reference for the console to generate the 3D ultrasound image by stitching together the plurality of ultrasound images, starting from the point of reference,
        wherein the ultrasound probe connector includes a braided tubing encapsulating the optical fiber, the braided tubing configured to provide a mechanical integrity to the optical fiber; and
    the console including one or more processors and non-transitory computer readable medium having logic stored thereon that, when executed by the one or more processors, causes performance of operations including:
        transmitting and receiving optical signals along the one or more core fibers;
        determining a shape of the one or more core fibers;
        acquiring the plurality of ultrasound images;
        identifying and tracking the one or more anatomical targets within the plurality of ultrasound images;
        determining ultrasound probe movement based on the shape of the one or more core fibers in combination with tracking the one or more anatomical targets;
        associating the ultrasound probe movement with the plurality of ultrasound images; and
        generating the 3D ultrasound image from the plurality of ultrasound images.

2. The system according to claim 1, wherein the one or more core fibers include a plurality of sensors distributed along a longitudinal length of a corresponding core fiber and each sensor of the plurality of sensors is configured to reflect a light signal of a different spectral width based on received incident light, and change a characteristic of the reflected light signal for use in determining a physical state of the optical fiber.

3. The system according to claim 1, wherein the optical fiber is a single-core optical fiber and wherein an incident light is provided in pulses.

4. The system according to claim 1, wherein the optical fiber is a multi-core optical fiber including a plurality of core fibers, and wherein an incident light propagates along a first core fiber and a reflect light signal propagates along a second core fiber.

5. The system according to claim 1, wherein determining ultrasound probe movement includes using the shape of the one or more core fibers taken in relation to the ultrasound probe.

6. The system according to claim 1, wherein determining the shape of the one or more core fibers includes using the transmitted and received optical signals.

7. The system according to claim 1, wherein associating the ultrasound probe movement with the plurality of ultrasound images includes associating the plurality of ultrasound images with the shape of the one or more core fibers taken in relation to the ultrasound probe.

8. The system according to claim 1, wherein generating the 3D ultrasound image includes using ultrasound images associated with the shape of the one or more core fibers taken in relation to the point of reference.

9. The system according to claim 1, wherein the optical fiber is centrally located within the braided tubing.

10. The system according to claim 1, wherein the braided tubing includes a mesh construction having a spacing between intersecting conductive elements of the braided tubing that is selected based on a degree of rigidity desired for the ultrasound probe connector.

11. The system according to claim 1, wherein the one or more anatomical targets include one or more of veins, arteries, bones, tendons, ligaments, or nerves.

12. The system according to claim 1, wherein:
the ultrasound probe further includes one or more electromagnetic sensors configured to measure a strength of a magnetic field generated by a magnet attached to a patient, the strength of the magnetic field related to a position of the ultrasound probe with respect to the magnet, and
the operations further include:
receiving magnetic strength values from the one or more electromagnetic sensors; and
associating each of the magnetic strength values with the plurality of ultrasound images.

* * * * *